US010537382B2

(12) United States Patent
Boudreaux et al.

(10) Patent No.: US 10,537,382 B2
(45) Date of Patent: Jan. 21, 2020

(54) SURGICAL INSTRUMENT WITH LATCHING TRIGGER LOCKOUT

(71) Applicant: Ethicon Endo-Surgery, LLC, Guaynabo, PR (US)

(72) Inventors: Chad P. Boudreaux, Cincinnati, OH (US); Gregory A. Trees, Loveland, OH (US); Geoffrey S. Strobl, Williamsburg, OH (US)

(73) Assignee: Ethicon LLC, Guaynabo, PR (US)

( * ) Notice: Subject to any disclaimer, the term of this patent is extended or adjusted under 35 U.S.C. 154(b) by 670 days.

(21) Appl. No.: 15/192,534

(22) Filed: Jun. 24, 2016

(65) Prior Publication Data

US 2017/0367752 A1    Dec. 28, 2017

(51) Int. Cl.
*A61B 18/14* (2006.01)
*A61B 17/00* (2006.01)
*A61B 18/00* (2006.01)

(52) U.S. Cl.
CPC ............ *A61B 18/1445* (2013.01); *A61B 2017/00371* (2013.01); *A61B 2017/00424* (2013.01); *A61B 2018/0063* (2013.01); *A61B 2018/1455* (2013.01)

(58) Field of Classification Search
CPC ........ A61B 18/1445; A61B 2018/1455; A61B 2018/0063; A61B 2017/00367; A61B 2017/00371
See application file for complete search history.

(56) References Cited

U.S. PATENT DOCUMENTS

| 5,480,409 A * | 1/1996 | Riza ................. A61B 17/2909 606/205 |
| 2003/0018331 A1 | 1/2003 | Dycus et al. |
| 2011/0087212 A1 | 4/2011 | Aldridge et al. |
| 2011/0087220 A1* | 4/2011 | Felder ............... A61B 18/1445 606/42 |
| 2012/0078139 A1 | 3/2012 | Aldridge et al. |
| 2012/0080332 A1 | 4/2012 | Shelton, IV et al. |
| 2012/0116379 A1 | 5/2012 | Yates et al. |

(Continued)

OTHER PUBLICATIONS

International Search Report and Written Opinion for International App. No. PCT/US2017/038920 (18 pages).

*Primary Examiner* — Michael F Peffley
*Assistant Examiner* — Amanda L Zink
(74) *Attorney, Agent, or Firm* — Mintz Levin Cohn Ferris Glovsky and Popeo, P.C.

(57) ABSTRACT

Instruments and methods for providing selective surgical instrument trigger lockout are provided herein. In one embodiment, a surgical instrument can include a distal end effector, a proximal actuator portion, a first trigger, a second trigger, and a lock arm. The lock arm can be configured to move between a first position, in which it interferes with actuation of the first trigger, and a second position, in which it permits actuation of the first trigger. Further, actuation of the second trigger can be effective to move the lock arm from the first position to the second position. Actuation of the first trigger can therefore be prevented if the second trigger is not already actuated. Selective trigger lockout can be useful in a variety of instruments, including, for example, surgical instruments that grasp, seal, and transect tissue.

7 Claims, 19 Drawing Sheets

(56) References Cited

U.S. PATENT DOCUMENTS

2013/0053831 A1\* 2/2013 Johnson ............ A61B 17/2909
                                              606/1
2015/0201953 A1   7/2015 Strobl et al.
2015/0209573 A1   7/2015 Hibner et al.
2015/0282824 A1  10/2015 Trees et al.

\* cited by examiner

SURGICAL INSTRUMENT WITH LATCHING TRIGGER LOCKOUT

FIELD

This disclosure relates generally to surgical instruments and, more particularly, to such instruments that include multiple actuating triggers or other control mechanisms.

BACKGROUND

A variety of surgical instruments are employed in various open, endoscopic, and laparoscopic surgeries. One group of such instruments is utilized to manipulate tissue, seal or staple tissue, and/or transect tissue. These instruments can include a distal end effector having opposed jaw members that move relative to one another to grasp tissue therebetween. Certain of these instruments can also include a cutting mechanism that can be advanced through the grasped tissue to transect it. Electrical or other energy can also be delivered to the grasped tissue to seal the tissue prior to, or concurrent with, transection. For example, electrical energy can be applied to the grasped tissue by various mono-polar and bi-polar radio frequency (RF) electrodes or other energy delivery structures coupled to the jaw members.

These surgical instruments often include a proximal actuator portion from which the distal end effector can be controlled. The proximal actuator portion can include a plurality of triggers or other control mechanisms to control the various functions of the instrument. For example, a first trigger can control the opening or closing of the jaw members to grasp tissue, while a second trigger can control the operation of a cutting mechanism and/or the delivery of energy to seal tissue. In use, a user can actuate the first trigger and latch it in an actuated or closed position to securely grasp and compress tissue between the first and second jaw members, then the user can actuate the second trigger to transect and/or seal the tissue.

The separate control triggers or other control mechanisms of the instrument can be susceptible to user error, however. For example, a user might actuate the second trigger (e.g., to transect and/or seal tissue) before fully actuating and/or latching the first trigger (e.g., to securely clamp tissue between the jaw members). Alternatively, a user might inadvertently release the first trigger while the second trigger is still being actuated, thereby releasing the grasped tissue as it is being transected and/or sealed. These actions can result in an incomplete or non-existent tissue seal and/or transection. This is because sufficient compression is important to both forming a good seal and facilitating passage of the cutting mechanism through the tissue.

Accordingly, there is a need for surgical instruments that include a trigger lockout feature to prevent actuation of a first trigger until such time as a second trigger is properly actuated. There is also a need for surgical instruments that prevent the release of an actuated first trigger until such time as the second trigger is fully released.

SUMMARY

The present disclosure generally provides instruments and methods for selectively providing trigger lockout for surgical instruments having multiple triggers or other control mechanisms. The instruments and methods described herein can prevent the actuation of a first trigger until such time as a second trigger is properly actuated and/or latched in a closed position. Further, the instruments and methods described herein can prevent the release of the first trigger from an actuated and/or latched position until such time as the second trigger is fully released. In a surgical instrument configured to grasp, seal, and transect tissue using a jaw closure trigger and a cutting mechanism and/or tissue sealing firing trigger, this can mean, e.g., preventing actuation of the firing trigger until the closure trigger is fully actuated and secured in the closed or actuated position. This can also mean preventing the release of the closure trigger until the firing trigger is fully released, meaning the cutting and/or sealing process has completed.

The instruments and methods disclosed herein generally accomplish such selective trigger lockout by providing a linkage or other mechanism between the multiple triggers of the instrument. The linkage or other mechanism can be configured to block the actuation of, for example, a second trigger, until a first trigger is moved to an actuated or closed position. Movement to such a position by the first trigger can cause movement of the linkage to a position that allows the second trigger to be actuated without interference. Accordingly, the actuation of one trigger can be made dependent upon the position or actuation status of another trigger. While such a mechanism can be suited to use with the tissue grasping, sealing, and transecting instruments described above, the principles described herein can also be applied to a variety of other instruments having multiple triggers or other control mechanisms.

In one aspect, a surgical instrument can include a distal end effector, a proximal actuator portion, a first trigger coupled to the proximal actuator portion, a second trigger coupled to the proximal actuator portion, and a lock arm coupled to the proximal actuator portion. The lock arm can be configured to move between a first position, in which it interferes with actuation of the second trigger, and a second position, in which it permits actuation of the second trigger. Moreover, actuation of the first trigger can be effective to move the lock arm from the first position to the second position.

The instruments and methods described herein can have a number of additional features and/or variations, all of which are within the scope of the present disclosure. In some embodiments, for example, release of the first trigger can be effective to return the lock arm from the second position to the first position. In such a configuration, actuation of the second trigger can be prevented whenever the first trigger is not already actuated. Further, the second trigger can be configured to interfere with the return of the lock arm from the second position to the first position until the second trigger is released. Accordingly, the first trigger can be prevented from releasing until after the second trigger is released. In one embodiment, the lock arm can include a ledge configured to ride along a shoulder of the second trigger to interfere with the return of the lock arm from the second position to the first position when the second trigger is being actuated.

The lock arm can be configured to move relative to other components of the instrument in a variety of manners. For example, in some embodiments the lock arm can be configured to rotate between the first position and the second position. In other embodiments, however, the lock arm can be configured to translate between the first position and the second position.

In certain embodiments, the surgical instrument can further include a latch that is coupled to the lock arm and configured to be received by a catch coupled to the first trigger. The latch can be pivotably coupled to the proximal actuator portion and biased toward a resting position. Further, the catch coupled to the first trigger can be configured to move the latch away from the resting position as the latch is received by the catch. Still further, movement of the latch away from the resting position can cause movement of the lock arm from the first position to the second position.

In still other embodiments, a surgical instrument can include a latch plate coupled to the proximal actuator portion, the latch, and the lock arm. Moreover, the latch plate can be configured to move relative to the proximal actuator portion from a released position to a latched position when the latch is received by the catch. Such movement can be of any known variety. For example, in some embodiments the latch plate can be configured to pivotably move relative to the proximal actuator portion. Still further, in some embodiments the movement of the latch plate from the released position to the latched position can cause movement of the lock arm from the first position to the second position.

In certain embodiments, the latch plate can be biased toward the released position. The biasing of a movable latch plate can eliminate any possibility of inadvertent actuation during transition between latched and unlatched states, as movement of the lock arm can be controlled by movement of the latch plate that occurs only after the latch is fully received by the catch.

A number of surgical instruments having multiple triggers can make use of the selective trigger lockout described herein. In one embodiment, for example, a distal end effector of a surgical instrument can include a first jaw member, a second jaw member, and a cutting element. The first and second jaw members can be configured to move between an open configuration and a closed configuration to clamp tissue therebetween. The cutting element can be configured to transect the tissue clamped between the first and second jaw members. Moreover, in some embodiments actuation of the first trigger can be configured to move the first and second jaw members from the open configuration to the closed configuration and actuation of the second trigger can be configured to distally translate the cutting member. In some embodiments, the distal end effector can be further configured to deliver radio frequency (RF) energy to tissue clamped between the first and second jaw members.

In another aspect, a surgical instrument can include a distal end effector configured to releasably grasp tissue, delivery radio frequency (RF) energy to grasped tissue, and transect the grasped tissue. The instrument can further include a proximal actuator portion, a first trigger coupled to the proximal actuator portion and configured to control grasping of tissue by the distal end effector, and a second trigger coupled to the proximal actuator portion and configured to control transecting the grasped tissue by the distal end effector. The instrument can also include a first latch component coupled to the proximal actuator portion, a second latch component coupled to the first trigger, and a lock arm coupled to the first latch component and configured to move between a first position, in which the lock arm interferes with actuation of the second trigger, and a second position, in which the second trigger can be actuated while clearing the lock arm. Further, the first latch component and the second latch component can be configured to contact one another such that the first trigger is retained in a closed position and the lock arm is retained in the second position.

As with the instrument described above, a number of variations and additional features are possible. For example, in some embodiments the instrument can further include a latch plate coupled to the proximal actuator portion, the first latch component, and the lock arm. The latch plate can be configured to move relative to the proximal actuator portion from a released position to a latched position when the first latch component and the second latch component contact one another. In certain embodiments, movement of the latch plate from the released position to the latched position can cause movement of the lock arm from the first position to the second position.

Surgical methods are also disclosed herein. Such methods can include, for example, actuating a first trigger of a surgical instrument to move first and second jaw members of the surgical instrument from an open configuration to a closed configuration to clamp tissue therebetween. The method can further include latching the first trigger to retain the first trigger in an actuated position and to move a lock arm from a first position, in which the lock arm blocks movement of a second trigger of the surgical instrument, to a second position, in which the lock arm permits movement of the second trigger. The method can also include actuating the second trigger to transect tissue clamped between the first and second jaw members.

In some embodiments, a surgical method can further include releasing the second trigger and unlatching the first trigger to release the first trigger from the actuated position and to move the lock arm from the second position to the first position. Moreover, in some embodiments interference between a shoulder of the second trigger and a ledge of the lock arm can prevent unlatching the first trigger until after releasing the second trigger.

Any of the features or variations described above can be applied to any particular aspect or embodiment of the disclosure in a number of different combinations. The absence of explicit recitation of any particular combination is due solely to the avoidance of repetition in this summary.

BRIEF DESCRIPTION OF THE DRAWINGS

FIG. 10B is a perspective view of the latching plate of the surgical instrument of FIG. 10A;

FIG. 10C is a perspective view of the lock arm of the surgical instrument of FIG. 10A;

DETAILED DESCRIPTION

Figure 1:
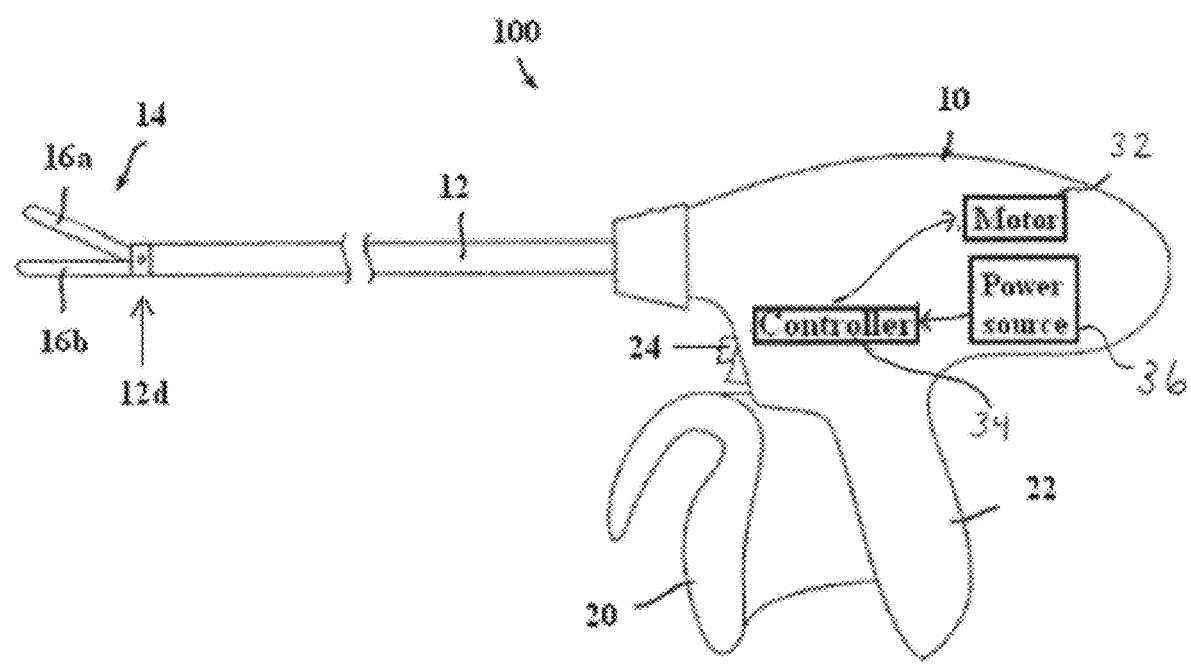
FIG. 1 is a side view schematic of a prior art surgical instrument including an end effector for grasping, sealing, and transecting tissue.

Certain exemplary embodiments will now be described to provide an overall understanding of the principles of the structure, function, manufacture, and use of the instruments and methods disclosed herein. One or more examples of these embodiments are illustrated in the accompanying drawings. Those skilled in the art will understand that the instruments and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present application. To the extent features are described herein as being a "first feature" or a "second feature," such numerical ordering is generally arbitrary, and thus such numbering can be interchangeable. Further, in the present disclosure, like-numbered components of the various embodiments generally have similar features when those components are of a similar nature and/or serve a similar purpose.

Additionally, the figures are not necessarily to scale and, to the extent that linear or circular dimensions are used in the description of the disclosed instruments and methods, such dimensions are not intended to limit the types of shapes that can be used in conjunction with such instruments and methods. A person skilled in the art will recognize that an equivalent to such linear and circular dimensions can easily be determined for any geometric shape. Still further, sizes and shapes of the instruments, and the components thereof, can depend at least on the anatomy of the subject in which the instruments will be used, the size and shape of components with which the instruments will be used, and the methods and procedures in which the instruments will be used.

Surgical instruments and methods are described herein that provide selective lockout of a trigger or other control mechanism based on a position or status of a different trigger or control mechanism. For example, in a surgical instrument that includes first and second triggers, e.g., for grasping and transecting tissue, respectively, the second trigger can be selectively prevented from actuating until the first trigger is fully actuated. Moreover, the first trigger can be prevented from releasing until the second trigger has been fully released. In such an instrument, by way of example, the selective trigger lockout can prevent the actuation of a cutting mechanism and/or the delivery of tissue sealing energy until the tissue is sufficiently grasped and/or compressed by the instrument. The trigger lockout can also prevent the release of compressive force on the grasped tissue until such time as the cutting mechanism and/or tissue sealing energy is finished acting on the grasped tissue. Such selective trigger lockout can be accomplished, for example, using a linkage or other mechanism that couples the multiple triggers or other control mechanisms of the instrument to prevent actuation and/or release of one trigger based on the position of another trigger.

FIG. 1 illustrates one embodiment of a surgical instrument 100 configured to grasp and cut tissue. The surgical instrument 100 can include a proximal actuator portion 10, a shaft portion 12, and a distal end effector 14 configured to grasp tissue. The proximal actuator portion 10 can be any type of pistol-grip or other type of handle known in the art that is configured to carry various actuators, such as actuator levers, triggers, or sliders that can control functionality of the end effector 14. In some embodiments, the proximal actuator portion 10 can also be configured for use with a robotic surgery platform, as opposed to a user's hand. As in the illustrated embodiment, the proximal actuator portion 10 can include a closure grip 20 and a stationary grip 22. Movement of the closure grip 20 toward and away from the stationary grip 22, such as by manual movement by a hand of a user, can adjust a position of the end effector 14. The shaft portion 12 can extend distally from the proximal actuator portion 10 and can have a bore (not shown) extending therethrough. The bore can carry mechanisms for actuating the end effector 14, such as a jaw closure tube and/or a drive shaft. The instrument 100 can be configured for purely mechanical user-powered operation via the use of various linkages, gear sets, etc. Alternatively, and as shown in FIG. 1, the instrument 100 can include one or more motors 32 (e.g., an electric motor) coupled to a power source 36 (e.g., a battery) and one or more controllers 34 (e.g., a digital data processor) that can provide power for operating the device in response to sensed actuation of one or more triggers or other control mechanisms.

Figure 2:
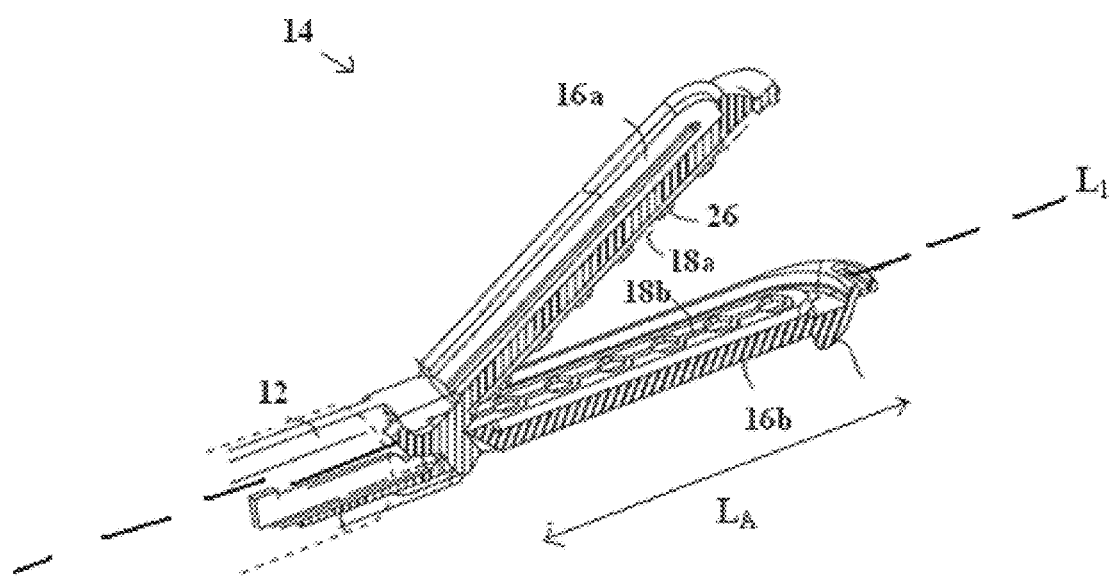
FIG. 2 is a perspective partial cross-sectional view of an end effector of the instrument of FIG. 1.

The end effector 14 can have a variety of sizes, shapes, and configurations. As shown in FIGS. 1 and 2, the end effector 14 can include a first, upper jaw 16a and a second, lower jaw 16b each disposed at a distal end 12d of the shaft portion 12. One or both of the upper and lower jaws 16a, 16b can be configured to close or approximate about a longitudinal axis $L_1$ of the end effector 14. Both of the jaws 16a, 16b can be moveable relative to the shaft portion 12 such that the end effector 14 can be moved between open and closed positions, or only one of the upper and lower jaws 16a, 16b can be configured to move relative to the shaft portion 12 and to the other of the jaws 16a, 16b so as to move the end effector 14 between open and closed positions.

When the end effector 14 is in the open position, the jaws 16a, 16b can be positioned at a distance apart from one another with space therebetween. In use, tissue can be positioned within the space between the jaws 16a, 16b. When the end effector 14 is in the closed position, a longitudinal axis of the upper jaw 16a can be substantially parallel to a longitudinal axis of the lower jaw 16b, and the jaws 16a, 16b can be moved toward one another such that the distance therebetween is less than when the end effector 14 is in the open position. In some embodiments, facing engagement surfaces 18a, 18b of the jaws 16a, 16b can be in direct contact with one another when the end effector 14 is in the closed position such that the distance therebetween is substantially zero. In the illustrated embodiment, the upper jaw 16a is configured to pivot relative to the shaft portion 12 and relative to the lower jaw 16b while the lower jaw 16b remains stationary. The jaws 16a, 16b can have a substantially elongate and straight shape, but a person skilled in the art will appreciate that one or both of the jaws 16a, 16b can be curved along the longitudinal axis $L_1$ of the end effector 14. The longitudinal axis $L_1$ of the end effector 14 can be parallel to and coaxial with a longitudinal axis of the shaft portion 12 at least when the end effector 14 is in the closed configuration and, if the end effector 14 is configured to articulate relative to the shaft portion 12, when the end effector 14 is not articulated relative to the shaft portion 12.

The jaws 16a, 16b can have any suitable axial length $L_A$ for engaging tissue, where the axial length $L_A$ is measured along the longitudinal axis $L_1$ of the end effector 14, as shown in FIG. 2. The axial length $L_A$ of the jaws 16a, 16b can also be selected based on the targeted anatomical structure for transection and/or sealing. In one embodiment, the jaws 16a, 16b can have a substantially equal axial length $L_A$, though use of different length jaws is possible in other embodiments.

The jaws 16a, 16b can have any number and any combination of features configured to facilitate grasping tissue between the facing surfaces 18a, 18b of the jaws 16a, 16b. The first and second engagement surfaces 18a, 18b can each be configured to directly contact tissue. Either one or both of the engagement surfaces 18a, 18b can include one or more surface features formed thereon that can help secure the tissue thereon. The one or more surface features can facilitate grasping of tissue, can be configured to increase friction between the tissue and the engagement surfaces 18a, 18b of the jaws 16a, 16b without tearing or otherwise damaging the tissue in contact with such surface features, and/or can facilitate forming substantially smooth, uniform layers of tissue. Examples of the surface features can include teeth, ridges, and depressions. In the illustrated embodiment of FIG. 2, the jaws 16a, 16b each include a plurality of teeth 26 positioned along an axial length of both of the engagement surfaces 18a, 18b.

One or both of the first and second jaws 16a, 16b can include one or more features configured to interact with a compression member (see FIG. 3) configured to apply compressive forces on tissue. For example, the first and second jaws 16a, 16b can include first and second recessed slots (not shown) that can receive portions of a compression member and act as a track to direct movement of the compression member. As another example, the first and second recessed slots can be configured to receive portions of a cutting element, as discussed further below.

Figure 3:
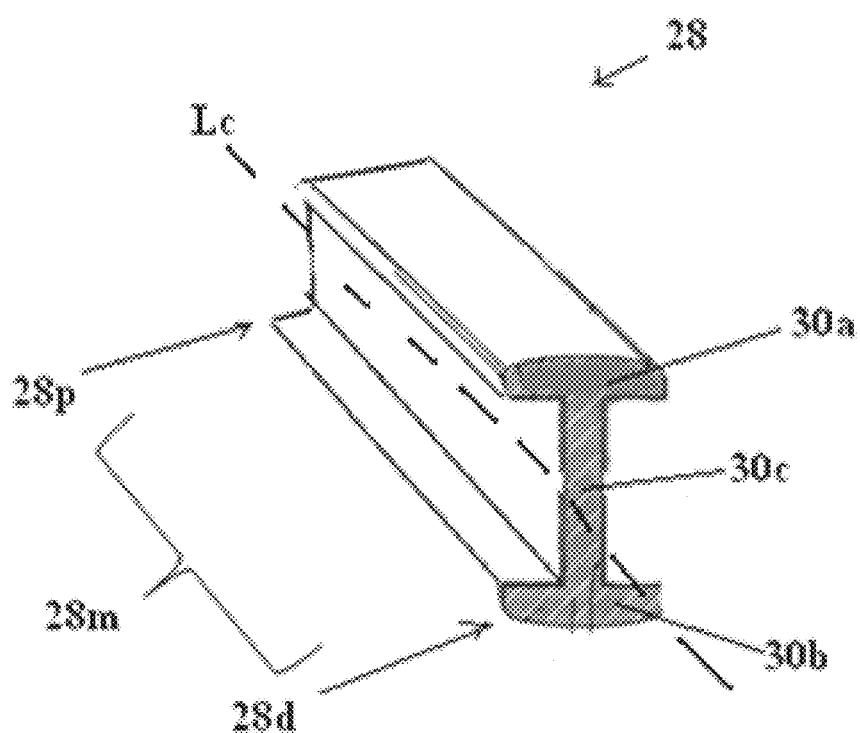
FIG. 3 is a detail view of a compression member of the instrument of FIG. 1.

The compression member mentioned above can have various sizes, shapes, and configurations. The compression member can have an elongate shape and can be moveable proximally and distally along the longitudinal axis $L_1$ of the end effector 14. One embodiment of a compression member 28 is illustrated in FIG. 3. As shown, the compression member 28 can have a proximal end 28p, a distal end 28d, and a medial portion 28m extending therebetween. The proximal end 28p and the medial portion 28m of the compression member 28 can be sized and shaped to reciprocate within the shaft portion 12 of the instrument 100. The distal end 28d of the compression member 28 can be sized and shaped to interact with the jaws 16a, 16b of the end effector 14. A longitudinal axis $L_C$ of the compression member 28 can be parallel to and coaxial with the longitudinal axis $L_1$ of the end effector 14, though other configurations are possible. The compression member 28 can be actuated from the proximal handle portion 10 of the instrument 100 by a firing actuator or trigger 24 that is operatively coupled to the proximal end 28p of the compression member 28, such as via a depressible button. Other examples of the firing actuator that can actuate the compression member include a lever, a knob, a switch, and a trigger. In general, the firing trigger 24 can be configured to be manually manipulated by a user to cause actuation of one or more other instrument elements, such as the compression member 28.

The compression member 28 can include a connecting portion 30c and upper and lower flanges 30a, 30b, thus providing an "I" cross-sectional shape for the compression member 28. As in the illustrated embodiment, the upper and lower flanges 30a, 30b can be positioned substantially perpendicular to the connecting portion 30c to form the "I" cross-sectional shape. The upper and lower flanges 30a, 30b can be sized and shaped to allow the upper and lower flanges 30a, 30b to slide in the above-mentioned recessed slots in the upper and lower jaw 16a, 16b, respectively. This sliding contact of lateral edges of the flanges 30a, 30b and sides of each of the recessed slots can prevent lateral flexing of the jaws 16a, 16b. The compression member 28 can have various other configurations. For example, the upper flange 30a can have a width that is greater than a width of the lower flange 30b, the widths being measured in a direction perpendicular to the longitudinal axis $L_1$ of the end effector 14.

The compression member 28 can form a distal tip of a drive shaft that moves through the end effector 14 such that only a distal portion of the drive shaft includes the compression member 28. A longitudinal length of the compression member 28 can be less than a longitudinal length of the end effector 14 such that the distal tip that includes the compression member 28 can move through the end effector 14 without the compression member 28 extending along the entire longitudinal length of the end effector 14. Alternatively, the compression member 28 can extend along an entire longitudinal length of the drive shaft. The compression member 28 can thus extend along the end effector's entire longitudinal length when the compression member 28 is in its distal-most position relative to the end effector 14.

The instrument 100 can include a cutting element (not shown) configured to cut tissue captured between the jaws 16a, 16b. The cutting element can have various sizes, shapes, and configurations. Examples of the cutting element include a knife blade and a sharp edge. The cutting element can be sized and shaped to cut various thicknesses and types of tissue positioned between the jaws 16a, 16b of the end effector 14. In an exemplary embodiment, the cutting element can be positioned at the distal end 28d of the compression member 28, such as by being formed on the connecting portion 30c of the compression member 28 as an integral part thereof, e.g., as a sharpened edge thereof, or as a member attached thereto, e.g., a blade mounted thereon. The cutting element can have a sharp or serrated edge configured to transect tissue. In an exemplary embodiment, the cutting element can be recessed relative to distal ends of upper and lower flanges 30a, 30b of the compression member 28, which can allow compression to occur prior to the cutting element cutting tissue as the compression member 28 traverses through the jaws 16a, 16b. In such an embodiment, the compression member 28 including a sharpened edge cutting element can form a cutting mechanism of the instrument 100 that can transect tissue disposed between the jaws 16a, 16b. In another embodiment, the cutting element can be configured such that it is not attached to the compression member 28, such that the cutting element can be configured to advance and retract relative to the jaws 16a, 16b so as to cut tissue sandwiched therebetween without applying compression to the tissue. In such an embodiment, the instrument 100 can include a separate compression member so that tissue engaged by the jaws 16a, 16b can still be compressed.

The surgical instrument 100 can include a second, closure actuator or trigger configured to open and close the jaws 16a, 16b of the end effector 14. Manipulation of the closure actuator, e.g., manual manipulation by a user, can cause the end effector 14 to move between the open and closed positions. In other words, manipulation of the closure actuator can cause one or both of the jaws 16a, 16b to pivot or otherwise move, as discussed above, so as to allow the jaws 16a, 16b to engage tissue, move anatomical structures, and/or perform other surgical functions. The closure actuator can have various sizes, shapes, and configurations. As in the illustrated embodiment, the closure actuator can include the closure grip 20 and the stationary grip 22. The closure grip 20 can be moveable toward and away from the stationary grip 22, such as via pivoting. The closure grip 20 can have a first position in which the closure grip 20 is angularly offset from the stationary grip 22 and in which the jaws 16a, 16b are open. The closure grip 20 can have a second position that is different from the first position and in which the closure grip 20 is positioned adjacent to, or substantially in contact with, the stationary grip 22 and in which the jaws 16a, 16b can engage tissue and apply a force to tissue disposed therebetween. The closure grip 20 can be biased to the first position with the jaws 16a, 16b being open, as shown in FIG. 1.

The closure grip 20 can be configured to move the jaws 16a, 16b between the open and closed positions using manual or powered components. In a manually actuated embodiment, the closure grip 20 can be coupled to a gear that interacts with a rack extending in the handle portion 10, and manual movement of the closure grip 20 toward the stationary grip 22 can move the rack distally toward the end effector 14, causing a force to be exerted onto the jaws 16a, 16b to close the jaws 16a, 16b. In addition to a gear and rack, however, a number of other mechanical linkages are also possible. In a powered embodiment, as shown in the illustrated embodiment of FIG. 1, the instrument 100 can include a motor 32, a controller 34, and a power source 36. The motor 32, the controller 34, and the power source 36 can be disposed in the proximal actuator portion 10. The motor 32 can include any type of motor (e.g., a rotary motor, etc.) configured for use with a surgical instrument, the controller 34 can include a variety of devices configured to process signals (e.g., a microprocessor, a central processing unit (CPU), a memory controller, etc.), and the power source 36 can include a variety of devices configured to supply power to at least the controller 34 (e.g., a battery, etc.). In some embodiments, the power source can be off-board instead of on-board the instrument 100, such as by the instrument 100 being attachable via wired connection to an electrical outlet or other power source. In some embodiments, the motor can be off-board instead of on-board the instrument 100, such as by being attachable via a wired connection to the motor. A manual movement of the closure grip 20 can be configured to cause the controller 34 to transmit a control signal to the motor 32, which can cause the jaws 16a, 16b to close via movement of the compression member 28. The closure grip 20 can interact with one or more locking features (not shown) configured to lock the closure grip 20 relative to the stationary grip 22. For example, the one or more locking features can automatically engage when the closure grip 20 substantially contacts the stationary grip 22.

The firing and closure actuators or triggers can cooperate to allow selective firing and closing of the instrument 100. The firing trigger 24 can be configured to be actuated to advance the cutting element through the end effector 14, apply energy to tissue, or both. Depressing or pivoting the firing trigger 24 can activate various elements in the instrument, and thereby cause one or more actions such as the compression member 28 and/or the cutting element advancing distally relative to the jaws 16a, 16b, and/or the compression member 28 and/or the cutting element retracting proximally relative to the jaws 16a, 16b, and/or energy being delivered to the jaws 16a, 16b. In a motor-powered embodiment, the firing trigger 24 can be in electrical communication with the motor 32 and the motor 32 can be operatively coupled to the compression member 28 using, e.g., a gear and rack. In such an embodiment, activation of the motor 32 can cause advancement and/or retraction of the compression member 28.

In a motor-powered embodiment, the instrument 100 can include at least one sensor (not shown) and the motor 32 can be configured to provide an output that is based at least in part on an output from the sensor. The controller 34 can be configured to determine an amount of power to be provided by the motor 32. The controller 34 can be configured to receive an output signal from the sensor, and based on the output signal from the sensor, cause the motor 32 to provide an output that supplies power to the cutting element. As discussed herein, the motor and the controller may not be disposed within the surgical instrument, e.g., may not be disposed within a handheld proximal actuator portion thereof. Instead, the motor and/or the controller can be located in a separate interface or within a generator to which the surgical instrument can be configured to operatively connect, as discussed further below. In other embodiments, however, the instrument can be manually powered by a user's movement of the various actuators or triggers using mechanical linkages to translate trigger movement into distal end effector operation.

The instrument 100 can also be configured to provide energy, e.g., radio frequency (RF) energy or other therapeutic treatment energy, to tissue clamped between the jaws 16a, 16b. The firing trigger 24 can be configured to cause application of the energy in some embodiments. The energy can be applied in a variety of manners. Examples of applying energy are described further in U.S. Pat. Pub. No. 2012/0078139, entitled "Surgical Generator For Ultrasonic And Electrosurgical Devices," filed Oct. 3, 2011; U.S. Pat. Pub. No. 2012/0116379, entitled "Motor Driven Electrosurgical Device With Mechanical And Electrical Feedback," filed Jun. 2, 2011; and U.S. application Ser. No. 14/166,194, entitled "Surgical Devices Having Controlled Tissue Cutting And Sealing," filed on Jan. 28, 2014, the entire contents of which are hereby incorporated by reference.

As discussed, for example, in previously mentioned U.S. Pat. Pub. No. 2012/0078139, entitled "Surgical Generator for Ultrasonic and Electrosurgical Devices," filed Oct. 3, 2011, RF energy is a form of electrical energy that may be in the frequency range of 300 kHz to 1 MHz. The instrument 100 can be configured to transmit low frequency RF energy through tissue, which causes ionic agitation, or friction, in effect resistive heating, thereby increasing the temperature of the tissue. Because a sharp boundary can be created between treated tissue and surrounding tissue, users of the instrument 100, e.g., surgeons and/or other medical professionals, can operate on the tissue with a high level of precision and control without sacrificing un-targeted adjacent tissue. The low operating temperatures of RF energy can be useful for removing, shrinking, or sculpting soft tissue while simultaneously sealing blood vessels. RF energy can work particularly well on connective tissue, which is primarily comprised of collagen and shrinks when contacted by heat. Heat generated by current flow from the RF energy through tissue to which the RF energy is applied can seal the tissue, e.g., form hemostatic seals within the tissue and/or between tissues, and can thus be particularly useful for sealing blood vessels, for example. When the instrument 100 includes a cutting element configured to cut tissue clamped between the jaws 16a, 16b and is configured to apply energy to tissue clamped between the jaws 16a, 16b so as to seal the tissue, the instrument 100 can be configured to separately cut and seal tissue clamped between the jaws 16a, 16b or can be configured to simultaneously cut and seal tissue clamped between the jaws 16a, 16b.

Figure 4:
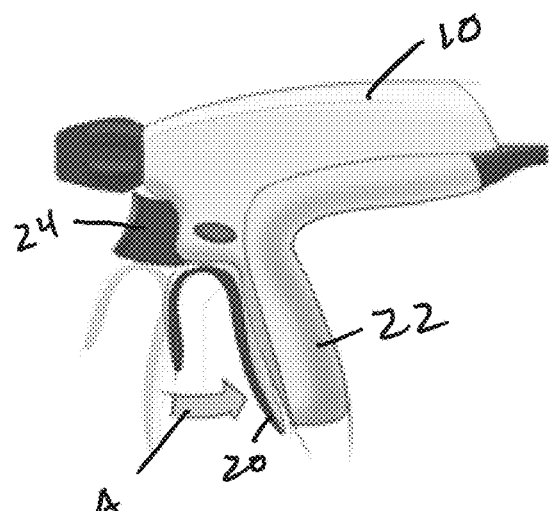
FIG. 4 is a partial side view of a prior art surgical instrument showing actuation of a closure trigger.
Figure 5:
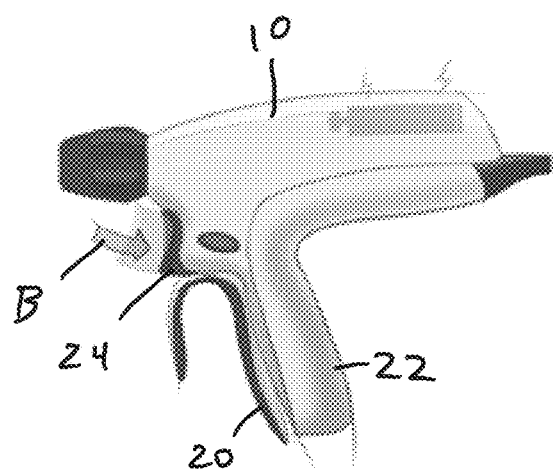
FIG. 5 is a partial side view of the surgical instrument of FIG. 4, with the closure trigger actuated, showing actuation of a firing trigger.
Figure 6:
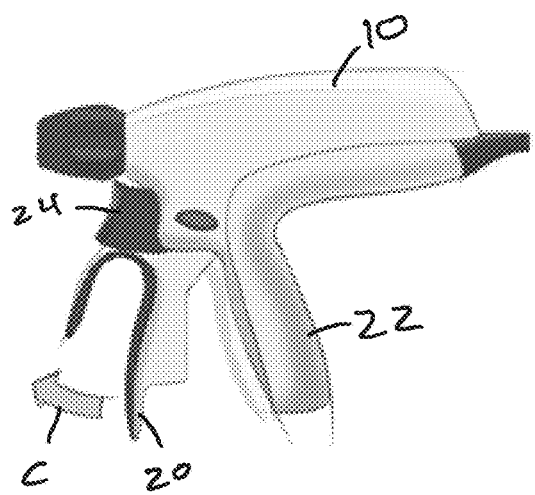
FIG. 6 is a partial side view of the surgical instrument of FIG. 4, showing release of the closure trigger.

As described in more detail below, FIG. 1 shows the instrument 100 in a first position in which the end effector 14 is in an open position with the jaws 16a, 16b being open with a distance of space therebetween. FIG. 4 shows the instrument 100 being moved to a second position from the first position in which the closure trigger 20 is being closed (moved along arrow A) so as to move the end effector 14 to a closed position where the jaws 16a, 16b are closed and clamp tissue therebetween. FIG. 5 shows the instrument 100 with the closure trigger 20 in an actuated/closed position and the firing trigger 24 is being actuated (moved along arrow B) to advance a cutting mechanism and/or deliver sealing energy. FIG. 6 shows the instrument 100 after the firing trigger 24 has been released and during release of the closure trigger 20 (movement along arrow C) to release the tissue grasped between the jaws 16a, 16b and return the instrument back to the first position shown in FIG. 1.

When the instrument 100 is in the first position, as shown in FIG. 1 and with the closure trigger 20 in shadow in FIG. 4, the closure trigger 20 is in an initial position in which the jaws 16a, 16b are open. When the closure trigger 20 is actuated, e.g., manually pulled proximally by a user's hand toward the stationary handle 22 as shown by the arrow A in FIG. 4, the jaws 16a, 16b can be closed so as to clamp tissue therebetween. The instrument 100 can be configured to latch or lock the closure trigger 20 in the closed position, such as by including a latch (not shown) on the stationary handle 22 configured to engage the closure trigger 20 when drawn close enough thereto so as to lock the closure trigger 20 in position relative to the stationary handle 22. Alternatively or in addition, the closure trigger 20 can be manually held closed by a user.

As shown in FIG. 5, the firing trigger 24 can be actuated, e.g., by being pressed by a user's finger as shown by a second arrow B, so as to cause transection and/or sealing of the tissue clamped between the jaws 16a, 16b by advancing a cutting mechanism and/or applying energy to the tissue.

Note that the delivery of sealing energy and the advancement of the cutting mechanism can be performed and controlled separately in some embodiments. This can be accomplished using an additional trigger, button, or other control mechanism, or the operations can be performed in a prescribed order by a controller responding to the actuation of the firing trigger 24. The tissue can thus be separately sealed and cut, with the sealing occurring before the cutting. Nonetheless, actuation of the firing trigger 24 can be configured to cause energy to be applied, which can provide for additional sealing of the tissue during cutting of the tissue to help reduce bleeding. The tissue can thus be simultaneously cut and sealed, even if the tissue was previously sealed.

If the instrument 100 includes a compression member, which as mentioned above can have the cutting element coupled thereto, the compression member can be configured to translate along the end effector 14 in response to actuation of the firing trigger 24. Actuation of the firing trigger 24 can thus allow further closure of the end effector 14 and allow for the jaws 16a, 16b to move closer together so as to more securely grasp tissue held therebetween. The further closure of end effector 14 can help compress the tissue between the jaws 16a, 16b and allow the energy to be more pointedly directed to the tissue between the jaws 16a, 16b, and/or can help prevent the energy from being applied to tissue before the jaws 16a, 16b have been sufficiently closed.

As shown in FIG. 6, after the tissue has been cut and sealed (separately and/or simultaneously), the closure trigger 20 can be released from its closed position so as to move back to its initial position, as shown by the arrow C. The closure trigger 20 can be released by being manually let go of by a user and/or by unlocking the closure trigger 20 (e.g., unlatching the latch).

As mentioned above, the configuration of the instrument 100 can be susceptible to user error in certain situations. For example, it can be possible for a user to actuate the firing trigger 24 before fully actuating the closure trigger 20, e.g., by engaging a latch (not shown) that secures the closure trigger in a closed/actuated position. Prematurely actuating the firing trigger 24 in this manner can result in an ineffective transection of tissue, as the tissue may be pushed out of the jaws 16a, 16b due to insufficient grip on the tissue. And, in embodiments in which RF or other energy is delivered in response to actuation of the firing trigger 24, an insufficient tissue seal can result. In other embodiments, a user may inadvertently release the closure trigger 20 while still actuating the firing trigger 24. This can produce similar effects on tissue transection and/or sealing.

FIGS. 7-22 illustrate various embodiments of surgical instruments that include latching trigger lockout mechanisms to selectively prevent the actuation and/or release of a trigger or other control mechanism based on the status or position of another trigger or other control mechanism. By preventing actuation and/or release of one trigger based on a position or actuation status of another trigger, users can be prevented from, e.g., actuating a firing trigger before a closure trigger is completely actuated, as well as releasing a closure trigger before a firing trigger is completely released.

Figure 7:
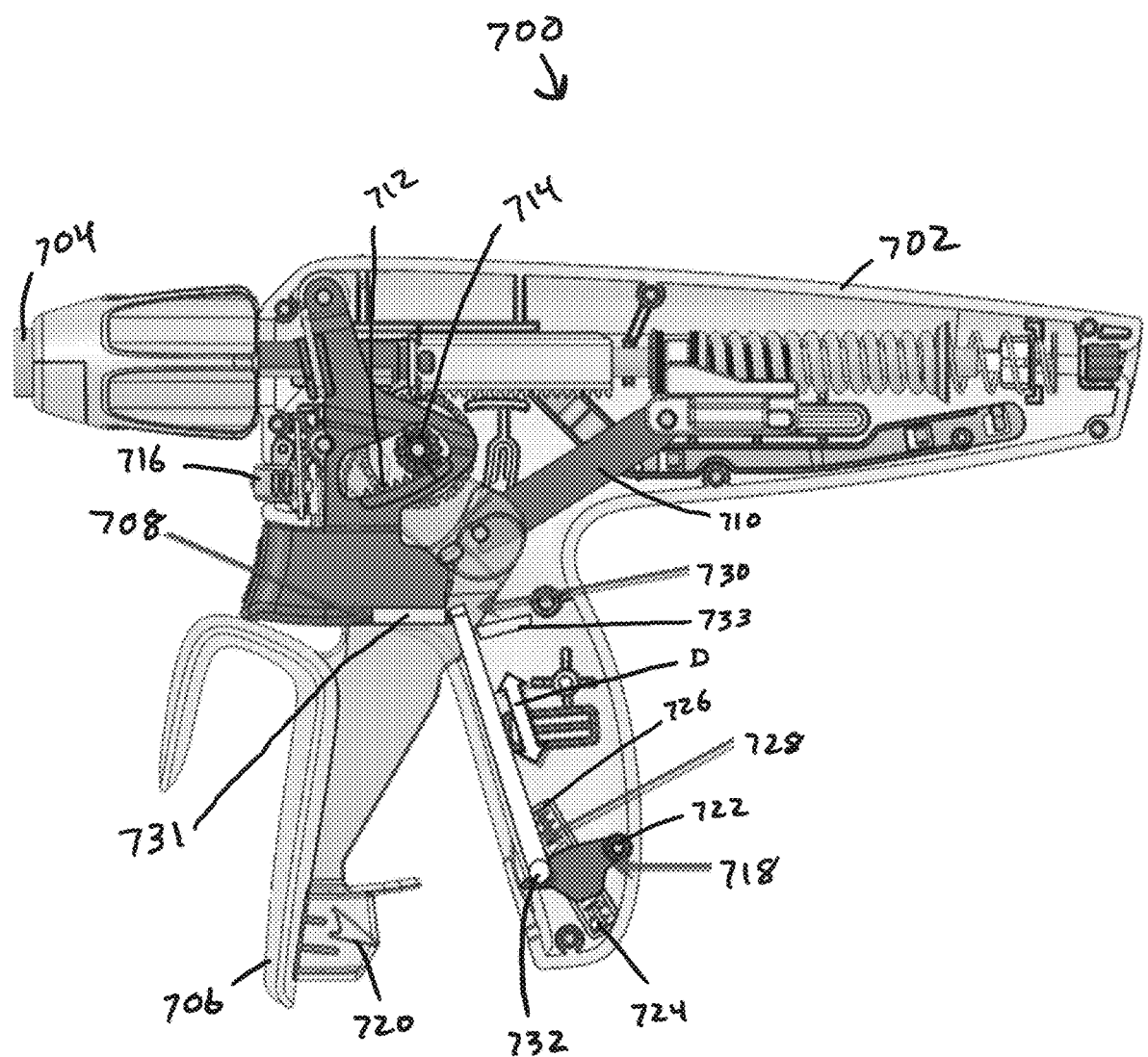
FIG. 7 is a partially transparent partial side view of one embodiment of a surgical instrument according to the teachings of the present disclosure.
Figure 8:
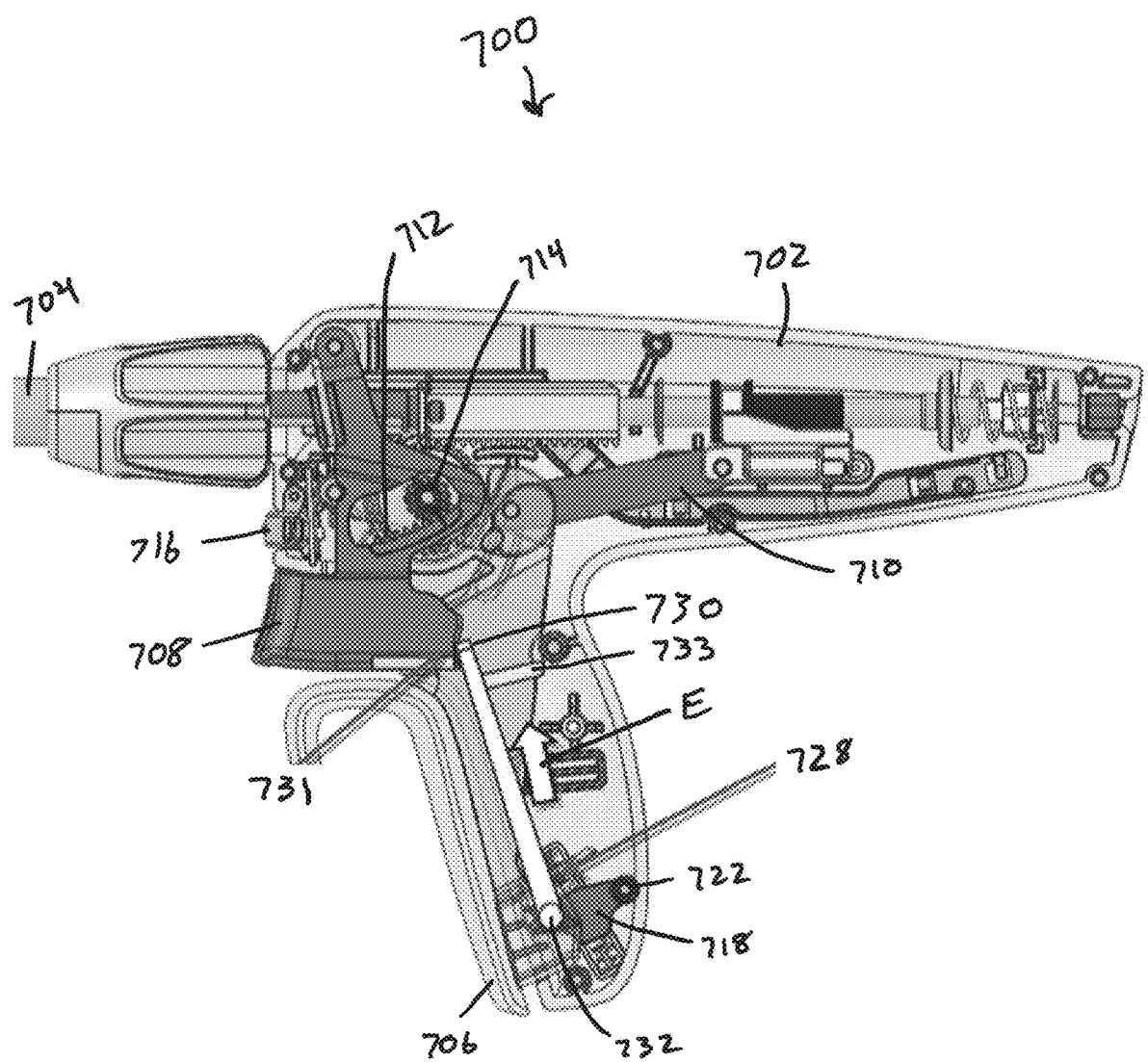
FIG. 8 is a partially transparent partial side view of the surgical instrument of FIG. 7 showing actuation of a closure trigger.
Figure 9:
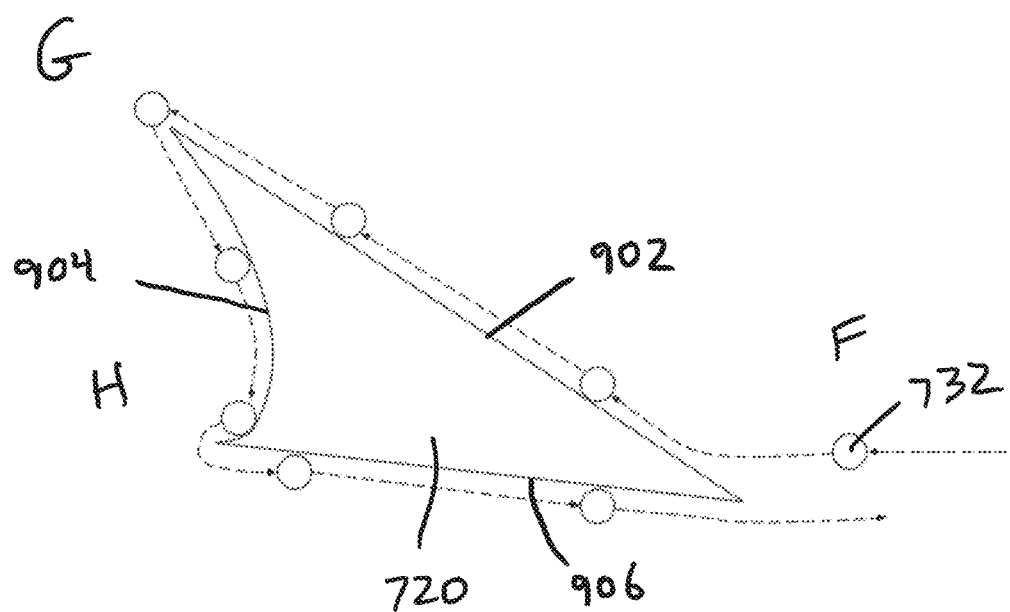
FIG. 9 is a side view of a latch catch of the surgical instrument of FIG. 7 showing travel of a latch therearound.

FIGS. 7-9 illustrate one embodiment of a surgical instrument 700 that is similar to the instrument 100 but includes a latching lockout mechanism to selectively prevent actuation of a tissue transection trigger based on a position of a jaw closure trigger. The instrument 700 can include a proximal actuator portion 702 and a shaft 704 extending to a distal end effector (not shown, see end effector 14 of FIGS. 1-2), similar to the instrument 100 described above. The instrument 700 can further include a first trigger 706 and a second trigger 708 that are both coupled to the proximal actuator portion 702. The first trigger 706 can be configured to move the first and second jaw members of the distal end effector between an open configuration and a closed configuration to clamp tissue therebetween, while the second trigger 708 can be configured to advance a cutting element through tissue grasped between the first and second jaw members to transect the tissue. Movement of the first trigger 706 can be communicated to the distal end effector using, e.g., mechanical linkage 710, and movement of the second trigger 708 can be communicated to a cutting element in the distal end effector via, e.g., rack 712 and gear 714. A variety of other configurations for transmitting movement of the first and second triggers 706, 708 to a distal end effector are known in the art and considered within the scope of the present disclosure.

While a variety of different configurations are possible, in the illustrated embodiment the instrument 700 includes a separate energy delivery trigger 716 coupled to the proximal actuator portion 702. The energy delivery trigger 716 can be configured to control the application of RF or other tissue sealing energy from at least a portion of the distal end effector. As noted above, in some embodiments the functionality of the energy delivery trigger 716 can be incorporated into the second trigger 708 such that the second trigger 708 activates energy delivery directly or indirectly (e.g., using a predetermined sequence of energy delivery and transection) via a digital data processor or other controller. In addition, while mechanical linkages 710, 712, and 714 are shown in the illustrated embodiment, in other embodiments movements of the first and second triggers 706, 708 can be sensed using one or more sensors known in the art and interpreted by one or more digital data processors acting as controllers. The one or more digital data processors can then control activation of one or more electric motors or other actuators to produce, e.g., distal end effector jaw member movement, cutting element advancement, or tissue sealing energy delivery.

The instrument 700 can include a latch mechanism for releasably securing the first trigger 706 in a fully actuated or closed position, as shown in FIG. 8. The latch mechanism can include a latch 718 coupled to the proximal actuator portion 702 of the instrument 700, as well as a complementary catch 720 coupled to the first trigger 706. In the illustrated embodiment, the latch 718 is pivotably coupled to the proximal actuator portion 702 of the instrument 700 via a pin 722, and is suspended in a neutral or resting position by a lower latch biasing element 724 and an upper latch biasing element 726. The lower and upper latch biasing elements can be, for example, coil springs or other elastically deformable members. A distal end of the latch 718 can include a protrusion, pin, or other feature 732 configured to be received by the catch 720 in order to secure the first trigger 706 in an actuated or closed position.

The pin 732 can also serve as a pivotable attachment point for a lock arm 728 that extends from the latch 718 to the second trigger 708 to provide selective trigger lockout for the first and second triggers 706, 708. More particularly, the lock arm 728 can be configured to translate upward or downward along arrow D in response to pivoting movement of the latch 718 about the pin 722. The lock arm 728 can be configured such that a lock stop 730 disposed at an end opposite from the pin 732 aligns with at least a portion of the second trigger 708 when the latch 718 is in a neutral or resting position balanced by the lower and upper latch biasing elements 724, 726. The lock stop 730 can include any of a variety of features, such as a laterally extending ledge shown in FIGS. 12, 13, and 16, that can be configured to interfere with movement of the second trigger 708 when in the position of FIG. 7. By way of further example, in the embodiment of FIG. 7 the lock stop 730 can be a ledge or other feature laterally extending from the lock arm 728 (e.g., extending normal to the plane of the page of the figure) that is configured to interfere with a shoulder 731 or other feature of the second trigger 708. Further, the lock arm 728 can be restrained from pivoting about the pin 732 toward a proximal end of the instrument 700 in response to an attempted actuation of the second trigger 708 by a rigid post 733. Accordingly, whenever the latch 718 is disposed in the neutral or resting position shown in FIG. 7, i.e., the position naturally assumed when the first trigger 706 is in an open or partially open configuration, actuation of the second trigger 708 can be prevented.

The catch 720 coupled to the first trigger 706 can be configured such that it displaces the pin 732 as it is received by the catch, which can pivot the latch 718 about the pin 722 against the biasing forces of the latch biasing elements 724, 726. In the illustrated embodiment, for example, the catch 720 can have a generally chevron-like shape defining a path therearound that the pin 732 travels during a complete latch/release cycle of the first trigger 706. FIG. 9 illustrates one embodiment of a path of the pin 732 around the catch 720 during a latch/release cycle of the first trigger 706. The pin 732 can first approach the catch 720 at position F in the figure and, as a user further urges the first trigger 706 toward a closed position, the pin 732 can be deflected upwards along the ramped surface 902 of the catch 720. When a user reaches the closed/actuated position of the first trigger 706, the pin 732 can be at position G extending distally beyond the ramped surface 902. Without the support of the ramped surface 902, the force of the lower and upper biasing elements 724, 726 can urge the latch to pivot downward about pin 722, thereby dropping the pin 732 toward position H in FIG. 9. Because the first trigger 706 can be biased toward an open configuration, the first trigger 706 can move slightly toward an open configuration as a user releases their grip, which can cause the pin 732 to ride along the surface 904 into a curved, grooved, or notched seat at position H. In such a position, the first trigger 706 is securely latched in a closed or actuated position.

Moreover, the position H can be offset (e.g., upward or downward) from the neutral or resting position F of FIG. 9 (note figure is not to scale) by varying an orientation of the catch 720. This means that, when the first trigger 706 is latched in a closed position, the latch 718 can be positioned upward or downward from the neutral or resting position shown in FIG. 7. In the illustrated embodiment, the latch 718 can be positioned above the neutral or resting position, as shown in FIG. 8. The displacement of the latch 718 from the neutral or resting position of FIG. 7 can cause a corresponding upward translation (e.g., along arrow E) of the lock arm 728 into the position shown in FIG. 8. In this position, the lock stop 730 can be positioned above the shoulder or other feature 731 formed on the second trigger 708 such that the ledge of the lock stop 730 clears the shoulder 731, thereby permitting actuation of the second trigger 708.

Still further, the ledge, protrusion, or other feature of the lock stop 730 can be configured to ride along the shoulder or other feature 731 of the second trigger when the second trigger is actuated. This relative arrangement can prevent any downward translation of the lock arm 728 during actuation of the second trigger 708, as the shoulder 731 would interfere with any downward movement of the lock stop 730. Maintaining the position of the lock arm 728 can prevent the latch 718 from pivoting downward about the pin 722, which in turn can prevent the release of the first trigger 706. As a result, the first trigger can be prevented from releasing until such time as the second trigger is fully released to clear any potential interference between the shoulder 731 and the lock stop 730.

To release the first trigger 706 back to the open configuration of FIG. 7 after the second trigger 708 is fully released, a user can urge the first trigger 706 toward the proximal actuator portion 702 such that the pin 732 again travels distally of a distal end of the catch 720. As shown in FIG. 9, once free from the curved seat of surface 904 the force of the lower and upper biasing elements 724, 726 can drive the latch down toward the neutral or resting position of FIG. 7, thereby allowing the pin 732 to ride along a bottom surface 906 of the catch 720 until the two components are separated from one another. The first trigger 706 can be moved toward an open position by a user's application of force or, in some embodiments, by a biasing force that can urge the first trigger 706 toward an open configuration when a user releases their grip. In addition, the bottom surface 906 can be angled such that the pin 732 is released from the catch 720 at a position displaced downward from the neutral or resting position, such that the latch biasing elements 724, 726 return the pin 732 to the starting position F once it is separated from the catch 720.

As the user releases and separates the latch 718 from the catch 720 and the latch returns to the neutral or resting position, the lock arm 728 can be translated back to the position shown in FIG. 7. In this position, actuation of the second trigger 708 is again prevented by interference between the lock stop 730 and the shoulder 731 of the second trigger 708. This completes a latch and release cycle of the first trigger 706 and the corresponding selective lockout of the second trigger 708.

The above described embodiment represents an improvement over prior devices, but there are still certain times during which the lockout mechanism can allow a user to inadvertently actuate the second trigger 708 before the first trigger is securely latched in a closed or actuated configuration. With reference to FIG. 9, for example, as the latch pin 732 travels up the final portion of the ramped surface 902 (e.g., left hand side of the figure) the latch 718 can be sufficiently displaced to clear the second trigger 708 lockout. However, during this time the first trigger 706 is not yet latched in a closed position because the latch pin 732 has not yet reached position G in FIG. 9, from where it will fall into the curved seat of surface 904. In other words, the user could release the first trigger 706 and it could return to the open configuration of FIG. 7.

In order to address this brief loss of trigger lockout, an alternative embodiment of a surgical instrument can be utilized. FIGS. 10A-16 illustrate such an embodiment of a surgical instrument 1000. The instrument 1000 can include a number of features that are similar to that of the instrument 700. These can include, for example, a proximal actuator portion 1002, a shaft 1004 extending to a distal end effector (not shown), a first trigger 1006, and a second trigger 1008. The instrument 1000 can also include a linkage 1010 coupling the first trigger to, for example, first and second jaw members of a distal end effector to control opening and closing thereof, as well as a gear rack 1012 and a gear 1014 coupling the second trigger 1008 to, for example, a cutting mechanism disposed in the distal end effector and configured to transect tissue grasped by the first and second jaw members. In addition, the instrument 1000 can include a separate energy delivery trigger 1016 similar to the trigger 716 of the instrument 700.

The instrument 1000 can include a different embodiment of a latch and trigger lockout mechanism, however. In particular, the instrument 1000 can include a latch 1018 coupled to the proximal actuator portion 1002 and a catch 1020 coupled to the first trigger 1006. And the latch 1018 can similarly be pivotably coupled via a pin 1022, but the pin 1022 can be coupled to a latching plate 1024 (shown in isolation in FIG. 10B) that is itself pivotably coupled to the proximal actuator portion 1002 via a pin 1026. This is in contrast to the direct coupling of the latch 718 to the proximal actuator portion 702 that is shown for the instrument 700.

Figure 10A:
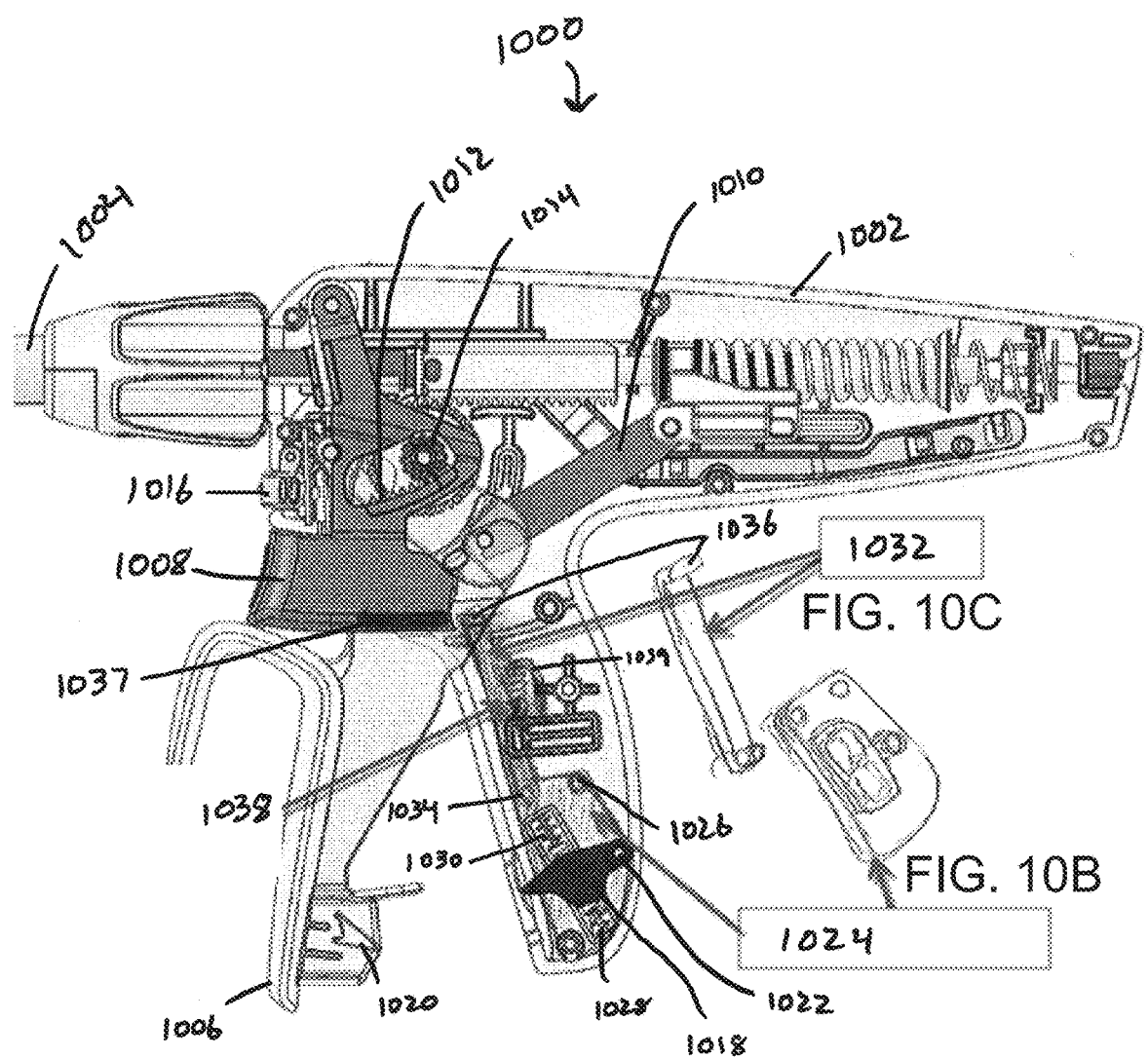
FIG. 10A is a partially transparent partial side view of one embodiment of a surgical instrument according to the teachings of the present disclosure.
Figure 11:
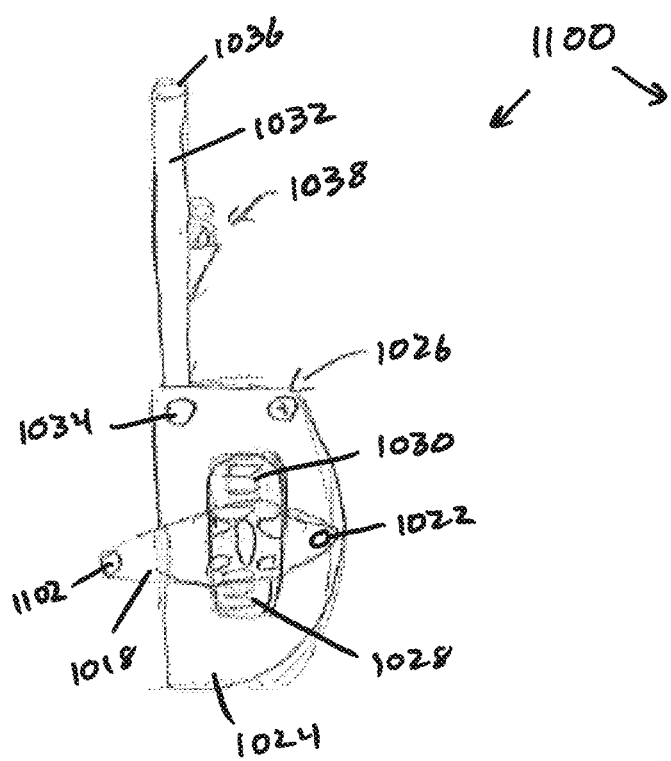
FIG. 11 is a side view of a latching trigger lockout mechanism of the surgical instrument of FIG. 10A.
Figure 12:
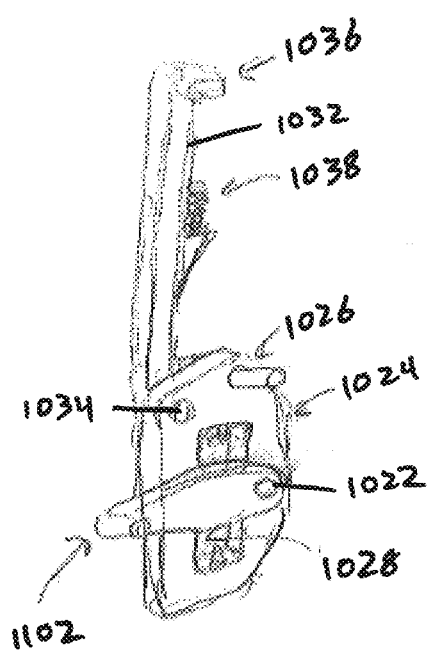
FIG. 12 is a perspective view of the latching trigger lockout mechanism of FIG. 11.

The latching plate 1024 can include recesses to house lower and upper latch biasing elements 1028, 1030 that act on the latch 1018 in a manner similar to the biasing elements 724, 726. The lockout mechanism also includes a lock arm 1032 (shown in isolation in FIG. 10C) that is pivotably coupled at one end to the latching plate 1024 by a pin 1034. At an opposite end of the lock arm 1032 can be a lock stop 1036 formed by a ledge or other feature, similar to the lock stop 730. The lock stop 1036 can be configured to selectively interfere with a shoulder or other feature 1037 in a similar manner as lock stop 730 and shoulder 731. In addition, a lock arm biasing element 1038 can be configured urge the lock arm 1032 in a downward direction, thereby urging the latching plate 1024 to pivot counter-clockwise (in the view of FIG. 10A) about the pin 1026. FIGS. 11 and 12 illustrate the various components of the trigger lockout mechanism 1100 in greater detail.

Similar to the instrument 700 described above, the lock arm 1032 can be configured to move between a first position, in which the lock arm interferes with actuation of the second trigger 1008, and a second position, in which the lock arm clears and permits actuation of the second trigger. FIG. 10A illustrates the instrument 1000 with its first trigger 1006 in an open position and the lock arm 1032 in the first position wherein actuation of the second trigger 1008 is prevented by interference between the ledge or other lock stop 1036 and the shoulder 1037.

Figure 13:
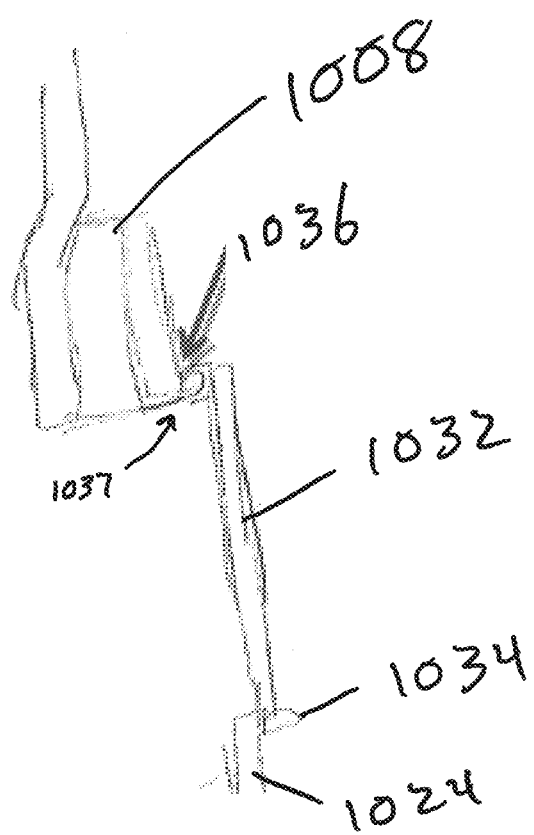
FIG. 13 is a rear view of a firing trigger and lock arm of the surgical instrument of FIG. 10A when the closure trigger is in an open position.

FIG. 12 shows a perspective view of the ledge that forms lock stop 1036 on the lock arm 1032. FIG. 13 illustrates a rear view of the interaction between the lock stop 1036 and the second trigger 1008 when in the configuration shown by FIG. 10A. As can be seen in FIG. 13, the lock arm 1032 is laterally offset from the second trigger 1008. The lock stop ledge or other feature 1036 formed on the lock arm 1032, however, extends laterally from the lock arm 1032 and is aligned with the shoulder or other feature 1037 formed on the second trigger 1008 such that the two components interfere with one another (i.e., movement of the second trigger out of the plane of the page in FIG. 13 would result in contact between the shoulder 1037 and the lock stop 1036). In such a configuration, any attempt to actuate the second trigger 1008 can be prevented by interference between the shoulder 1037 of the second trigger 1008 and the lock stop 1036 of the lock arm 1032. Note that the lock arm 1032 can be prevented from pivoting rearward in response to an attempted actuation of the second trigger 1008 by a post 1039 coupled to the proximal actuator portion 1002. The post 1039 can also serve as a support for the lock arm biasing element 1038, as shown in FIG. 10A.

In order to actuate the second trigger 1008, a user must first actuate the first trigger 1006 and latch it in a closed or actuated position. To do so, a user can urge the first trigger 1006 proximally toward the proximal actuator portion 1002 until a first latch component coupled to the proximal actuator portion, e.g., the latch 1018 of FIG. 10A, contacts a second latch component coupled to the first trigger 1006, e.g., the catch 1020 of FIG. 10A. The latch 1018 and catch 1020 can interact with one another in a manner similar to the latch 718 and the catch 720, including by making use of a multi-sided catch 1020 that can selectively displace the position of the latch 1018 from a neutral or resting position provided by lower and upper latch biasing elements 1028, 1030.

In the instrument 1000, however, displacement of the latch 1018 does not directly result in translation of the lock arm 1032. Rather, the latch 1018 can pivot upward or downward from its resting or neutral position without causing any change in the orientation of the latching plate 1024. Once the latch 1018, and in particular the distal latching pin 1102, is received in the curved seat of the catch 1020 and the first trigger 1006 is secured in a closed position, a user can release their grip on the first trigger 1006. The first trigger can be biased toward an open position by, for example, resistive force from tissue clamped between first and second jaw members of the distal end effector or, in some embodiments, by a biasing element (not shown). As the first trigger moves toward an open configuration while the latch 1018 is secured to the catch 1020, it can pivot the latching plate 1024 about the pin 1026 in the direction of arrow I against the force of biasing element 1038, as shown in FIG. 14.

The pivoting movement of the latching plate 1024 can cause translation of the lock arm 1032. As shown in FIG. 14, pivoting as the latching plate 1024 about the pin 1026 in the direction of arrow I (clockwise in the plane of the figure), the lock arm 1032 can be translated upward in the direction of arrow J. This upward translation of the lock arm 1032 can cause the lock stop 1036 to move above and clear the shoulder 1037 of the second trigger 1008, thereby allowing its actuation. This orientation can be seen in the side view of FIGS. 14 and 15, as well as the rear view of FIG. 16.

Figure 15:
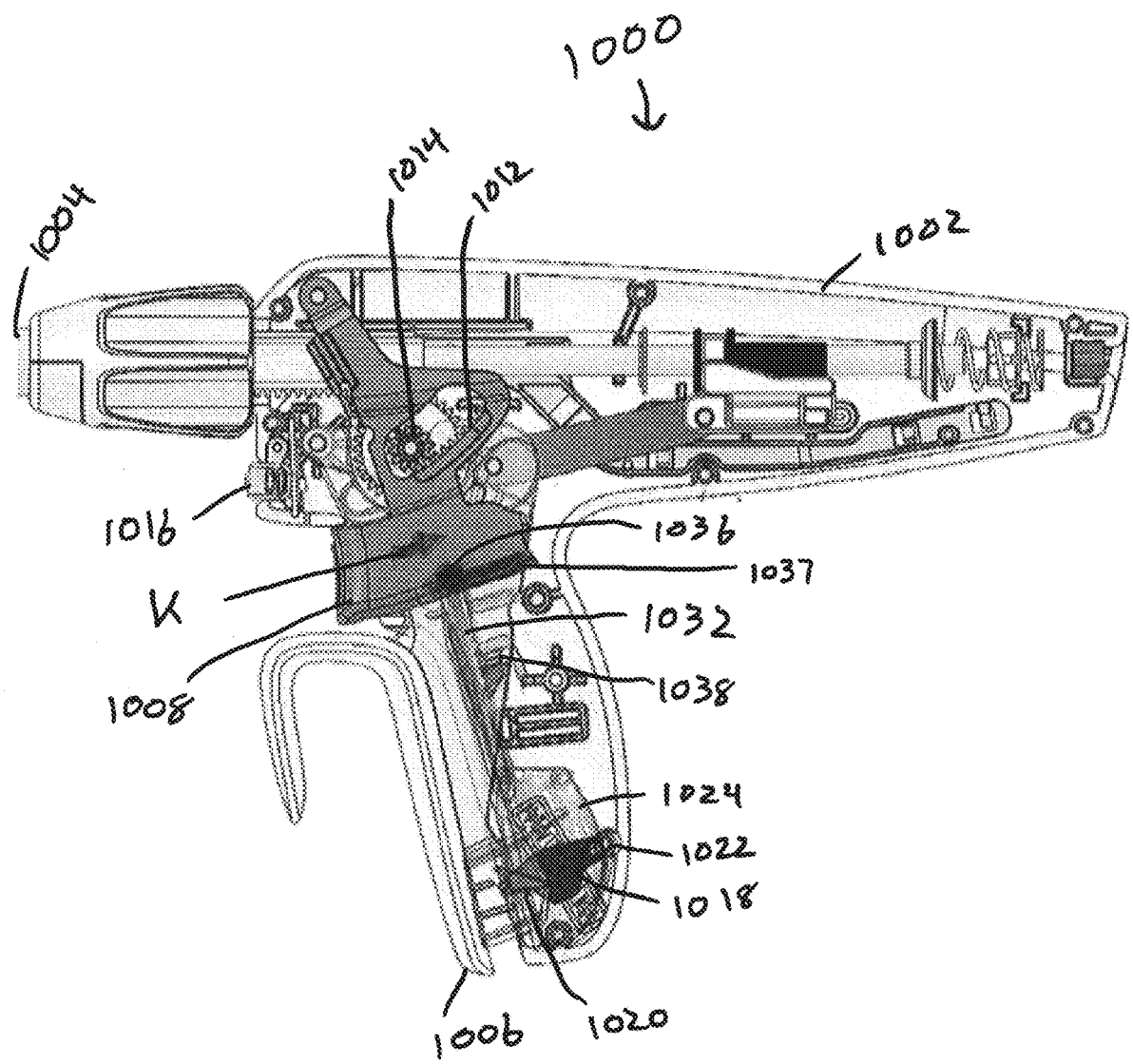
FIG. 15 is a partially transparent partial side view of the surgical instrument of FIG. 10A showing actuation of a firing trigger when the closure trigger is in a closed position.
Figure 16:
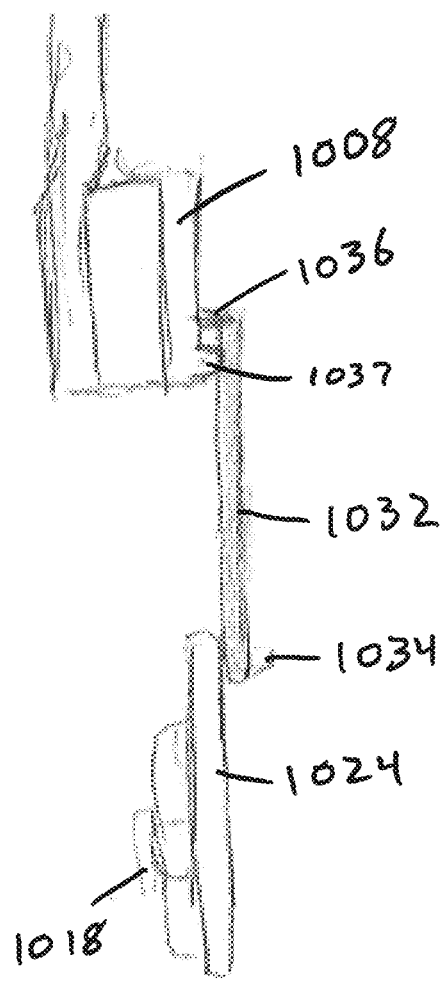
FIG. 16 is a rear view of a firing trigger and lock arm of the surgical instrument of FIG. 10A when the closure trigger is in a closed position.

As shown in FIG. 15, a user can actuate the second trigger 1008 by depressing it in the direction of arrow K to, for example, transect tissue clamped between the first and second jaws of the distal end effector. At all times during the throw or actuation of the second trigger 1008, the ledge or other lock stop 1036 can be disposed above the shoulder 1037 of the second trigger (see FIGS. 15 and 16) such that the lock arm 1032 is prevented from translating downward. Preventing movement of the lock arm 1032 in this manner can ensure that the latching plate 1024 remains in position and the first trigger 1006 remains latched in a closed position.

Figure 14:
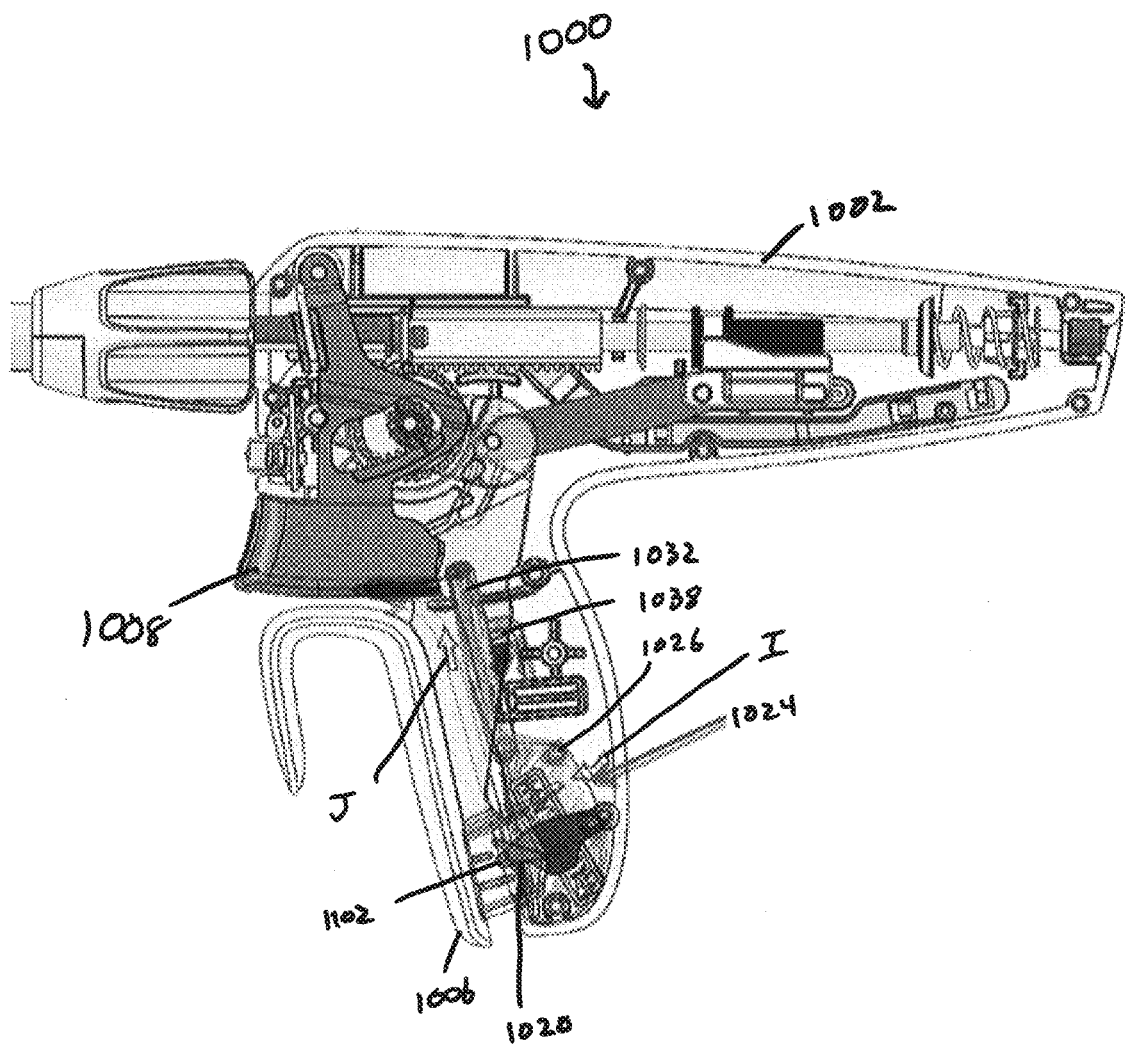
FIG. 14 is a partially transparent partial side view of the surgical instrument of FIG. 10A showing actuation of a closure trigger.

Only after the second trigger 1008 is released and returned to the position shown in FIG. 14 can the lock arm 1032 be clear to translate back to the position shown in FIG. 10A. To do so, a user can apply closing pressure to the first trigger 1006, which can aid the lock arm biasing element 1038 in translating the lock arm 1032 downward and pivoting the latching plate 1024 back to the position shown in FIG. 10A (i.e., pivoting the latching plate counter-clockwise in the plane of the figure). This movement can realign the lock stop 1036 with the shoulder 1037 of the second trigger 1008 to prevent actuation of the second trigger. Further application of closing pressure by the user to the first trigger 1006 can move the latching pin 1102 beyond a distal end of the catch 1020, which can cause the latching pin 1102 to release from the catch 1020, similar to how the latch pin 732 releases from the catch 720, as described above. Once the latching pin 1102 releases from the catch 1020, a user can release their grip and biasing force on the first trigger 1006 can return it to the open position or configuration shown in FIG. 10A.

The use of a pivoting latching plate 1024 as an intermediate linkage between the lock arm 1032 and the latch 1018 can provide an advantage in that there is no time during which the second trigger can be actuated while the first trigger is not fully actuated and latched. This is because the latching process of the first trigger is completed before any movement of the lock arm takes place. Indeed, pivoting the latching plate 1024 to cause movement of the lock arm 1032 depends upon successful coupling of the latch 1018 and catch 1020. Similarly, the latch 1018 cannot be released from the catch 1020 until after the lock arm 1032 has been returned to a position in which actuation of the second trigger 1008 is prevented.

Figure 17:
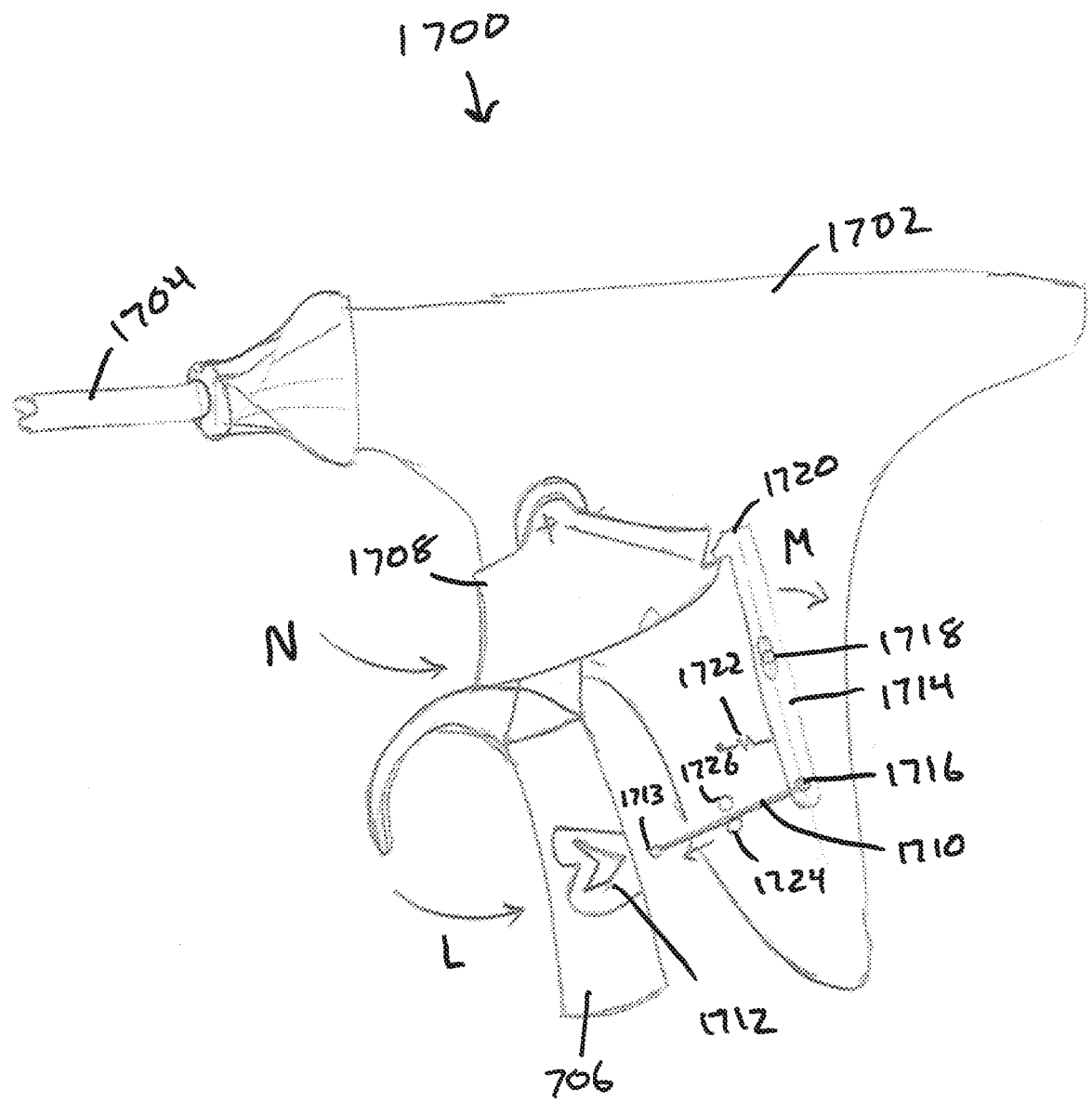
FIG. 17 is a partially transparent partial side view of one embodiment of a surgical instrument according to the teachings of the present disclosure.
Figure 18:
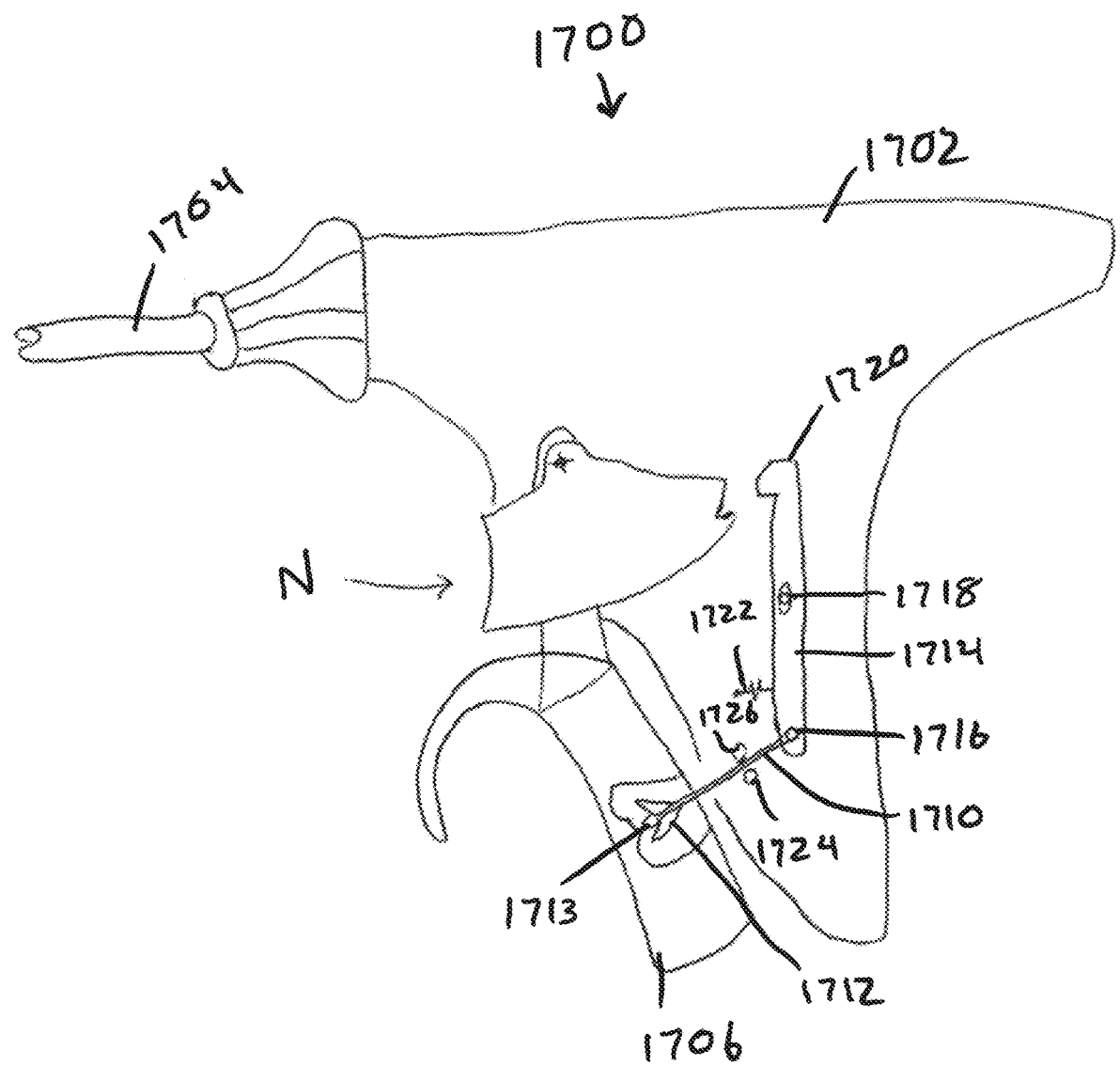
FIG. 18 is a partially transparent partial side view of the surgical instrument of FIG. 17 showing actuation of a firing trigger when a closure trigger is in a closed position.

The above described embodiments of a surgical instrument are not an exhaustive listing. FIGS. 17-22 show still further embodiments of surgical instruments with selective trigger lockout mechanisms. FIGS. 17 and 18, for example, illustrate an instrument 1700 in which a lock arm is configured to rotate—rather than translate—in and out of position blocking actuation of a second trigger. The instrument 1700 includes a number of features similar to the instruments 700 and 1000, including a proximal actuator portion 1702, a shaft 1704 extending to a distal end effector, a first trigger 1706 controlling a first functionality of the distal end effector, and a second trigger 1708 controlling a second functionality of the distal end effector.

Selective trigger lockout of the instrument 1700 can be accomplished using a latch 1710 or other first latch component coupled to the proximal actuator portion 1702 and a catch 1712 or other second latch component coupled to the first trigger 1706. In the illustrated embodiment, the latch 1710 can be a leaf spring or other semi-rigid member and can include a pin 1713 at one end thereof that is configured to be received by the catch 1712. At another end thereof, the latch 1710 can be coupled to a lock arm 1714 via a pin 1716. The lock arm 1714 can be pivotably coupled to the proximal actuator portion 1702 via a pin 1718 disposed along a mid-portion thereof and can include a lock stop 1720 formed at an end opposite from the pin 1716. The lock stop 1720 can be configured to engage with a complementary feature formed on or coupled to the second trigger 1708. In one embodiment, for example, the lock stop 1720 can be a hook or other feature formed on the lock arm 1714, while the second trigger 1708 can include a recess, pocket, shoulder, or other feature configured to interface with the lock stop.

As mentioned above, the lock arm 1714 can be pivotably coupled to the proximal actuator portion 1702 of the instrument 1700 such that it can rotate about the pin 1718. Further, a lock arm biasing element 1722 can urge the lock arm 1714 into a position in which it prevents actuation of the second trigger 1008, as shown in FIG. 17. The lock arm biasing element 1722 can be, for example, a coil spring, magnet, or other known biasing element.

To permit actuation of the second trigger 1708, a user can apply a closing force in the direction of arrow L to the first trigger 1706. As the first trigger 1706 nears the proximal actuator portion 1702, the pin 1713 at the distal end of the latch 1710 can be deflected by the catch 1712 in a manner similar to the latch 718 and catch 720 described above. Rather than a rigid latch 718 with lower and upper biasing elements 724, 726, however, the instrument 1700 can include a semi-rigid leaf spring latch 1710 and rigid lower and upper supports 1724, 1726 to produce similar behavior.

Once the pin 1713 at the distal end of the latch 1710 is received within a curved or notched seat of the catch 1712 (as shown in FIG. 18), a user can release their grip on the first trigger 1706 and allow a biasing force to urge the first trigger toward an open position. This slight movement of the first trigger 1706 while connected to the latch 1710 can pivot the lock arm 1714 in the direction of arrow M in FIG. 17 against the force of biasing element 1722. In this second position shown in FIG. 18, the lock arm 1714 can be clear of the second trigger path, thereby permitting its actuation. A user can then proceed to actuate the second trigger 1706 by applying force thereto in the direction of arrow N.

While the instrument 1700 does not include the ledge 1036 and shoulder 1037 of the instrument 1000, the rotating paths of the second trigger 1708 and the lock arm 1714 can be configured such that the first trigger 1706 cannot be released from its latched configuration unless the second trigger 1708 is in an open or released position. This is because the second trigger, if in an actuated position, can be configured to interfere with the lock arm 1714 returning to its initial position shown in FIG. 17.

To release the first trigger 1706, a user can apply further closure force to the first trigger. Initially, this can aid the biasing element 1722 in pivoting the lock arm 1714 back to the first position shown in FIG. 17. This return motion of the lock arm 1714 can reengage the lockout of the second trigger 1708 such that it cannot be actuated. Further application of closure force to the first trigger 1706 can advance the latch pin 1713 out of the grooved or curved seat of the latch 1712, and the elasticity of the leaf spring latch 1710 can cause the latch pin 1713 to move free of the catch 1712. The user can then release their grip and allow biasing force (again, from tissue clamped between the first and second jaws or from a biasing element disposed between the proximal actuator portion and the first trigger) to move the first trigger to an open position, as shown in FIG. 17.

The use of a pivoting lock arm 1714 and a lock arm biasing element 1722 can provide the same advantages of the instrument 1000 noted above, namely, the elimination of any point in time where the second trigger can be actuated while the first trigger is not securely latched in an actuated or closed position. Rather, the instrument 1700 can function similarly to the instrument 1000 in that latching of the first trigger in a closed position is accomplished before any movement of the lock arm 1714, and the lock arm 1714 is returned to its blocking position before the process of releasing the first trigger is initiated.

FIGS. 19-22 illustrate still another embodiment of a latching trigger lockout mechanism according to the teachings provided herein. The surgical instrument 1900 shown in these figures utilizes a unitary latch and lock arm component 1911 that is pivotably coupled to a proximal actuator portion 1902 of an instrument 1900. The latch and lock arm component 1911 is configured to interact with both a catch 1912 coupled to a first trigger 1904 and a second trigger 1908. Further, the latch and lock arm component 1911 can be biased via, e.g., a spring or other biasing element (not shown), toward the position labeled as 1911a in FIG. 19 and shown in FIG. 21.

Figure 19:
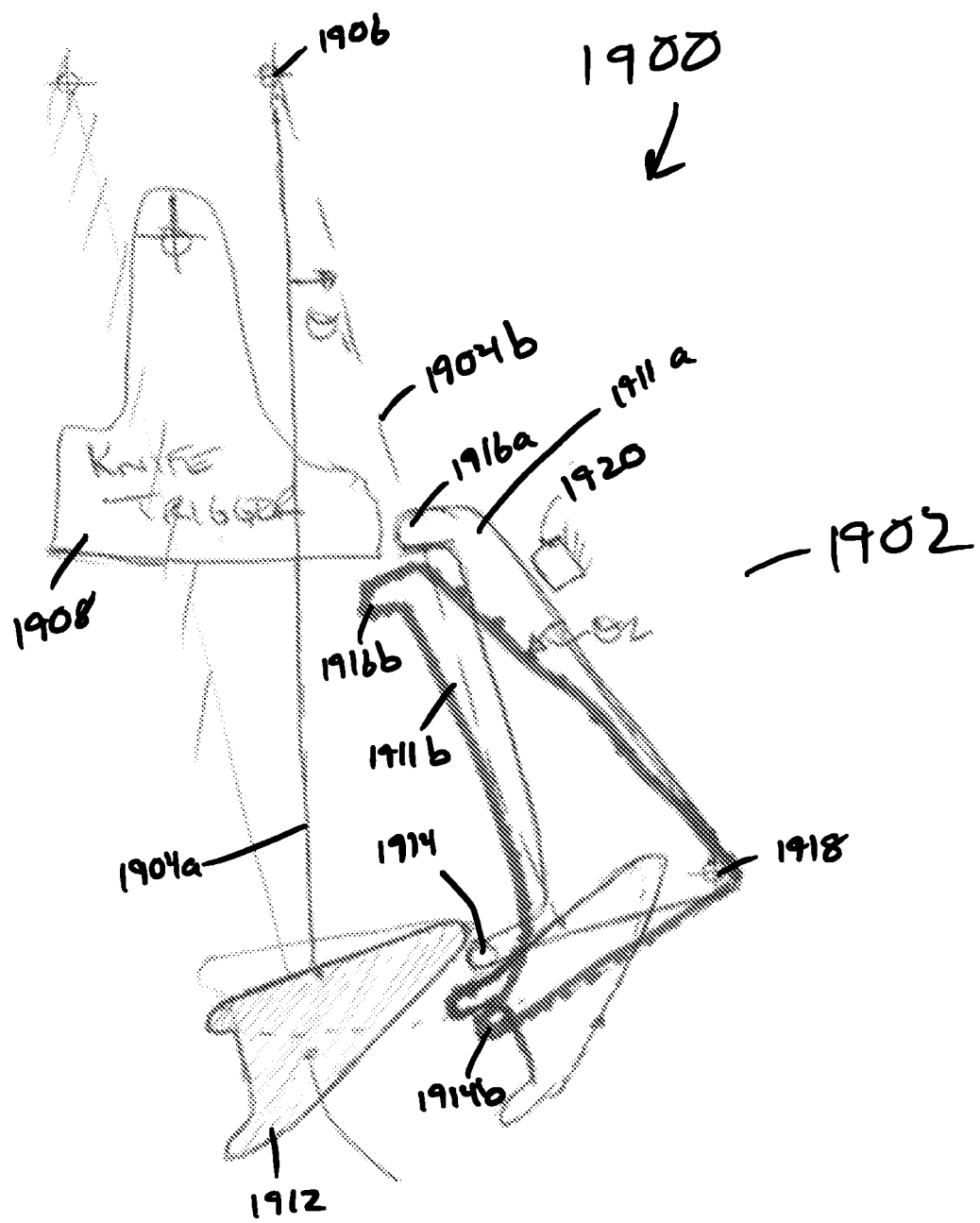
FIG. 19 is a partially transparent partial side view of one embodiment of a surgical instrument according to the teachings of the present disclosure illustrating various components of the instrument in two different positions.
Figure 21:
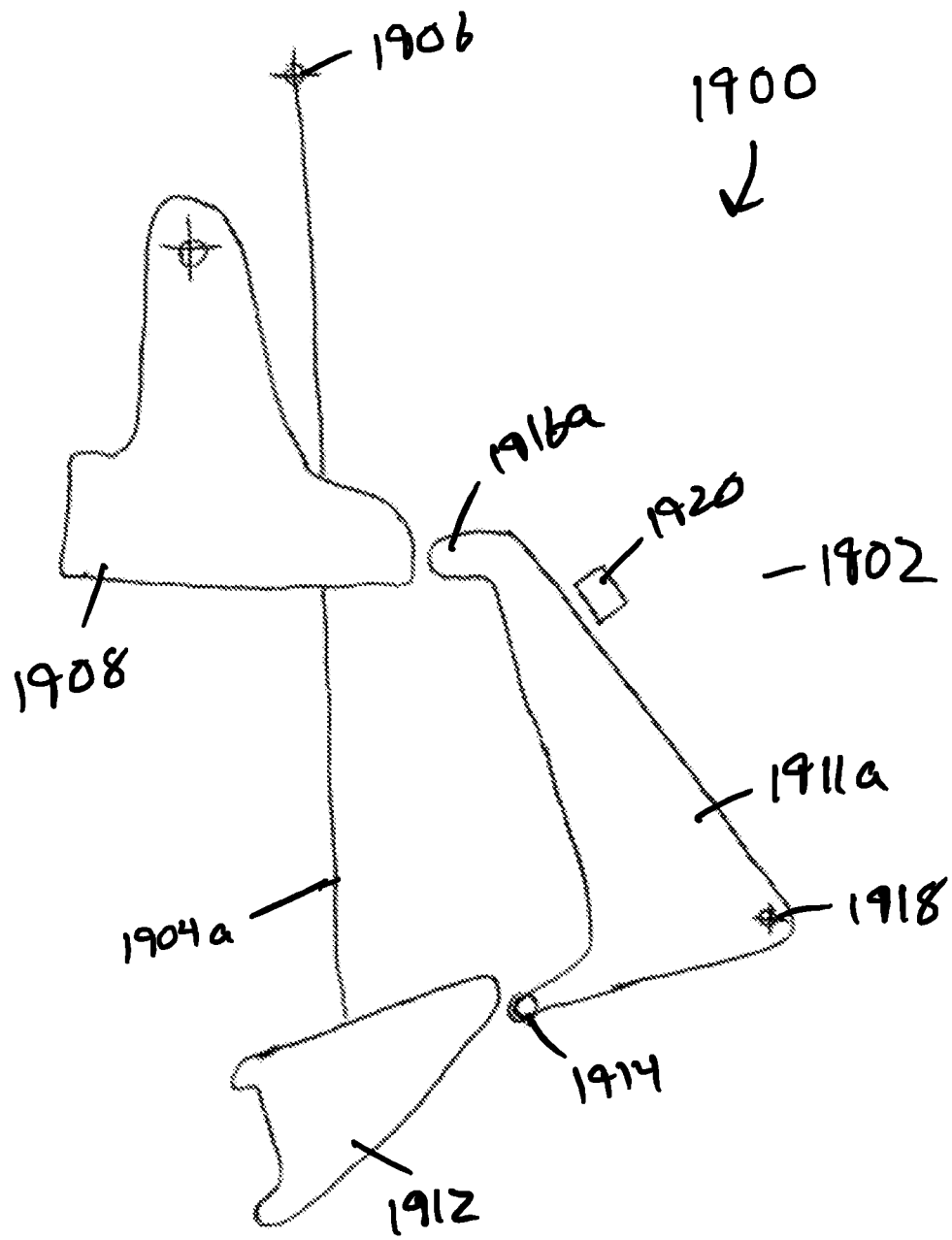
FIG. 21 is a partially transparent partial side view of the surgical instrument of FIG. 19 when the closure trigger is in an open position.

With reference to FIGS. 19 and 21, an initial configuration is shown in which the first trigger 1904 and the second trigger 1908 are in an open position (denoted by 1904a for the first trigger). The latch and lock arm component is in a first position identified as 1911a. In this configuration, a lock stop 1916 of the latch and lock arm component 1911 is positioned so as to prevent actuation of the second trigger 1908. Post 1920 can be coupled to the proximal actuator portion 1902 of the instrument 1900 and can prevent rotation of the latch and lock arm component 1911 about the pin 1918 if a user attempts to actuate the second trigger 1908.

Figure 20:
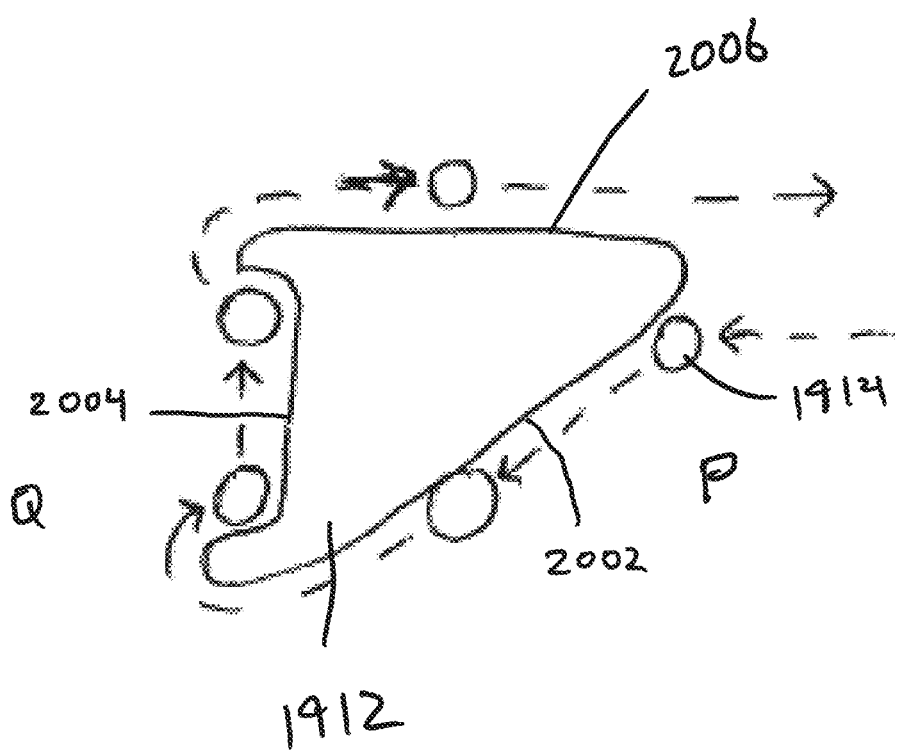
FIG. 20 is a side view of a latch catch of the surgical instrument of FIG. 19 showing travel of a latch therearound.
Figure 22:
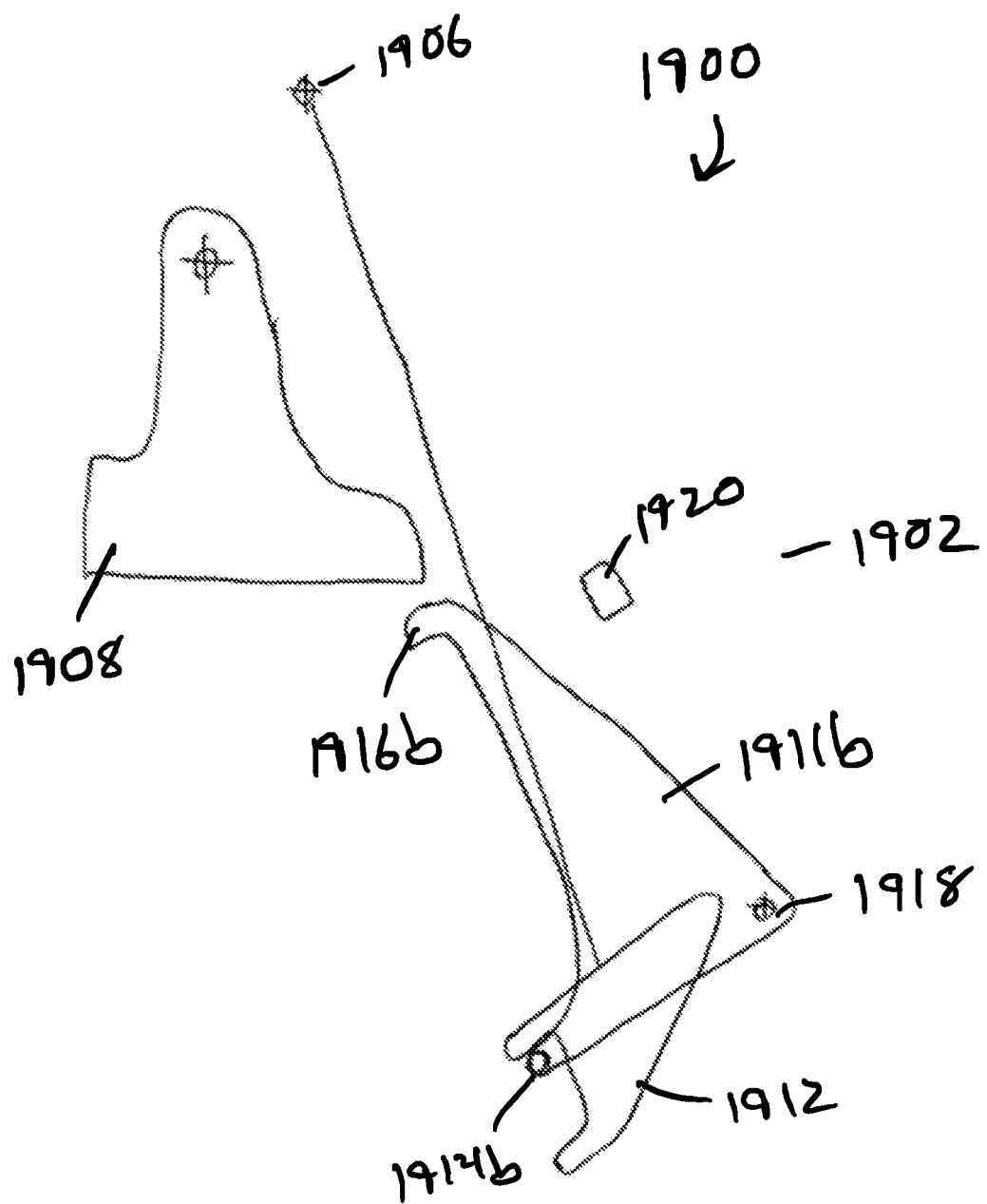
FIG. 22 is a partially transparent partial side view of the surgical instrument of FIG. 19 when the closure trigger is in a closed position.

As a user begins to actuate the first trigger 1904, thereby rotating it about pivot point 1906 into the configuration shown in FIG. 22 and denoted by 1904b, a latching pin 1914 coupled to the latch and lock arm component 1911 can engage with a catch 1912 coupled to the first trigger 1904. FIG. 20 illustrates one embodiment of how the latching pin 1914 can travel around, and be received by, the catch 1912. The latching pin 1914 can first contact the catch 1912 at position P and, as a user continues to move the first trigger 1904 through the angle θ1 from the position marked 1904a to the position marked 1904b, the latching pin 1914 can ride along the ramped surface 2002. As the latching pin 1914 rides along this surface 2002, the latch and lock arm component 1911 can be rotated about the pin 1918 through the angle θ2 from the position marked 1911a to the position marked 1911b. As this rotation occurs, the lock stop 1916 can move from the position marked 1916a, in which it blocks actuation of the second trigger 1908, to the position 1916b, in which it clears the movement path of the second trigger 1908. Note that the shape of the catch 1912 is substantially reversed from the orientation of the catch 720 described above in order to enable downward pivoting motion of the latch and lock stop component 1911. The orientation of the catch 720 could similarly be reversed to achieve reversed translation of the lock arm 728.

Similar to the latch and catch described above in connection with FIG. 9, the latching pin 1912 can be received within a grooved, notched, or curved surface 2004 of the catch 1912 once the first trigger 1904 is sufficiently closed and the latching pin 1912, reaches position Q of FIG. 20. This configuration, also shown in FIG. 19 at 1914b and in FIG. 22, retains the first trigger 1904 in a closed position (shown by position 1904b) and the latch and lock arm component 1911 in a position (labeled 1911b) that permits actuation of the second trigger 1908.

Moreover, the latch and lock arm component 1911 can be configured such that it cannot be returned to the initial position marked as 1911a until such time as the second trigger 1908 is fully released. Similar to the embodiments shown in FIGS. 17 and 18, if a user were to attempt to release the first trigger 1904 while actuating the second trigger 1908, the second trigger can be configured to interfere with movement of the latch and lock arm component 1911, thereby preventing the release of the first trigger 1904 until the second trigger 1908 is released and clears the movement path of the latch and lock arm component 1911.

Once the second trigger 1908 is released, a user can release the first trigger 1904 by applying closure force to the first trigger 1904. This can allow the latching pin 1914 to move beyond the curved, notched, or grooved surface 2004 and the biasing of the latch and lock arm component 1911 can rotate the latching pin 1914 up onto the surface 2006 of the catch 1912 shown in FIG. 20. The catch 1912 and latch and lock arm component 1911 can then separate, and biasing force can rotate the latch and lock arm component back into the position identified as 1911a where actuation of the second trigger 1908 is blocked.

Regardless of the particular instrument embodiment employed, a surgical method according to the present disclosure can include actuating a first trigger of a surgical instrument. In some embodiments, actuating the first trigger can move first and second jaw members of a surgical instrument from an open configuration to a closed configuration to clamp tissue therebetween. The method can further include latching the first trigger to retain the first trigger in an actuated position and to move a lock arm from a first position, in which the lock arm blocks movement of a second trigger of the surgical instrument, to a second position, in which the lock arm permits movement of the second trigger. The method can also include actuating the second trigger, which in some embodiments can transect tissue clamped between the first and second jaw members.

A surgical method can further include releasing the second trigger, as well as unlatching the first trigger to both release the first trigger from the actuated position and move the lock arm from the second position to the first position. As noted above, in some embodiments interference between a shoulder of the second trigger and a ledge or other lock stop of the lock arm can prevent unlatching the first trigger until after releasing the second trigger. Other surgical methods, including alternative orders of operating triggers, other control mechanisms, or similar components are also possible and considered within the scope of the present disclosure.

The instruments disclosed herein can be formed from a variety of materials and can have a variety of different sizes and shapes. For example, instruments or components thereof can be formed from various polymers and/or metals. Furthermore, particular components can be formed from different materials than other components. By way of further example, a proximal actuator portion can be formed from a polymer material, (e.g., polycarbonate), while an end effector can be formed from a metal, such as surgical grade stainless steel (e.g., 17-4), other 300 and 400 series stainless steels, titanium, and aluminum, perhaps to take advantage of greater rigidity. Of course, these are just non-limiting examples of possible material combinations. Instrument sizes can also vary greatly, depending on the intended use and surgical site anatomy.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces, and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present disclosure.

The instruments described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the instrument due to the materials utilized, the presence of electrical components, etc.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A surgical instrument, comprising:
a distal end effector;
a proximal actuator portion;
a first trigger coupled to the proximal actuator portion;
a second trigger coupled to the proximal actuator portion;
a lock arm in direct contact with the second trigger;
wherein the lock arm is configured to move between a first position in which the lock arm in direct contact with the second trigger interferes with actuation of the second trigger, and a second position in which the lock arm in direct contact with the second trigger permits actuation of the second trigger;
wherein actuation of the first trigger is effective to move the lock arm from the first position to the second position;
wherein release of the first trigger is effective to return the lock arm from the second position to the first position;
wherein the second trigger is configured to interfere with the return of the lock arm from the second position to the first position until the second trigger is released; and
wherein the lock arm includes a ledge configured to ride along a shoulder of the second trigger to interfere with the return of the lock arm from the second position to the first position when the second trigger is being actuated.

2. A surgical instrument, comprising:
a distal end effector configured to releasably grasp tissue, deliver radio frequency (RF) energy to grasped tissue, and transect the grasped tissue;
a first trigger configured to control grasping of tissue by the distal end effector;
a second trigger configured to control transecting the grasped tissue by the distal end effector;
a first latch component disposed within a stationary pistol grip handle that is coupled to the first and second triggers;
a second latch component coupled to the first trigger; and
a lock arm extending from the first latch component and through the stationary pistol grip handle, the lock arm being configured to move between a first position in which the lock arm interferes with actuation of the second trigger, and a second position in which the second trigger can be actuated while clearing the lock arm;
wherein the first latch component and the second latch component are configured to contact one another such that the first trigger is retained in a closed position and the lock arm is retained in the second position.

3. The instrument of claim 2, further comprising:
a latch plate coupled to the stationary pistol grip handle, the first latch component, and the lock arm;
wherein the latch plate is configured to move relative to the stationary pistol grip handle from a released position to a latched position when the first latch component and the second latch component contact one another.

4. The instrument of claim 3, wherein movement of the latch plate from the released position to the latched position causes movement of the lock arm from the first position to the second position.

5. A surgical method, comprising:
actuating a first trigger of a surgical instrument to move first and second jaw members of the surgical instrument from an open configuration to a closed configuration to clamp tissue therebetween;
latching the first trigger to a stationary pistol grip handle to retain the first trigger in an actuated position and to move a lock arm that extends through the stationary pistol grip handle from a first position, in which the lock arm blocks movement of a second trigger of the surgical instrument, to a second position, in which the lock arm permits movement of the second trigger; and
actuating the second trigger to transect tissue clamped between the first and second jaw members.

6. The method of claim 5, further comprising:
releasing the second trigger; and
unlatching the first trigger to release the first trigger from the actuated position and to move the lock arm from the second position to the first position.

7. The method of claim 6, wherein interference between a shoulder of the second trigger and a ledge of the lock arm prevents unlatching the first trigger until after releasing the second trigger.

* * * * *